US007118893B2

(12) United States Patent
Ranum et al.

(10) Patent No.: US 7,118,893 B2
(45) Date of Patent: *Oct. 10, 2006

(54) SCA7 GENE AND METHODS OF USE

(75) Inventors: Laura P. W. Ranum, St. Paul, MN (US); Michael D. Koob, Roseville, MN (US); Melinda L. Moseley-Alldredge, St. Paul, MN (US); Kellie A. Benzow, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 197 days.

This patent is subject to a terminal disclaimer.

(21) Appl. No.: 10/357,322

(22) Filed: Feb. 3, 2003

(65) Prior Publication Data

US 2003/0180768 A1    Sep. 25, 2003

Related U.S. Application Data

(60) Continuation of application No. 09/684,843, filed on Oct. 6, 2000, now Pat. No. 6,514,755, which is a division of application No. 09/135,994, filed on Aug. 18, 1998, now Pat. No. 6,280,938.

(60) Provisional application No. 60/056,170, filed on Aug. 19, 1997.

(51) Int. Cl.
*C12P 19/34* (2006.01)

(52) U.S. Cl. .................... 435/91.2; 435/91.2

(58) Field of Classification Search ............... 435/6, 435/91.1, 91.2; 536/23.1, 24.3, 24.33
See application file for complete search history.

(56) References Cited

U.S. PATENT DOCUMENTS

| 4,683,194 A | 7/1987 | Saiki et al. |
| 4,683,195 A | 7/1987 | Mullis et al. |
| 5,741,645 A | 4/1998 | Orr et al. |
| 5,834,183 A | 11/1998 | Orr et al. |
| 6,280,938 B1 | 8/2001 | Ranum et al. |
| 6,514,755 B1 | 2/2003 | Ranum et al. |
| 6,524,791 B1 | 2/2003 | Ranum et al. |

FOREIGN PATENT DOCUMENTS

| WO | 95/01437 | 1/1995 |
| WO | 97/42314 | 11/1997 |

OTHER PUBLICATIONS

Lindblad et al., "An Expanded CAG Repeat Sequence in Spinocerebellar Ataxia Type 7," *Genome Research*, Oct. 1996, vol. 6, pp. 965-971.*
Benomar et al., "The gene for autosomal dominant cerebellar ataxia with pigmentary macular dystrophy maps to chromosome 3p12-p21.1." *Nature Genetics*, 1995, vol. 10, Abstract only.*
Altschul et al., "Basic local alignment search tool," *J. Mol. Biol.*, 215(3):403-410 (1990).

Benomar et al., "The gene for autosomal dominant cerebellar ataxia with pigmentary macular dystrophy maps to chromosome 3p12-p21.1." *Nature Genetics*, 10, 84-88 (1995).
Brook et al., "Molecular basis of myotonic dystrophy: Expansion of a trinucleotide (CTG) repeat at the 3' end of a transcript encoding a protein kinase family member," *Cell*, 68(4):799-808 (1992). AND erratum appears in *Cell*, 69(2):385 (1992).
Buxton et al., "Detection of an unstable fragment of DNA specific to individuals with myotonic dystrophy," *Nature*, 355(6360):547-548 (1992).
Campuzano et al., "Friedreich's ataxia: autosomal recessive disease caused by an intronic GAA triplet repeat expansion," *Science*, 271(5254):1423-1427 (1996).
Cheng et al., "Clinical evidence of genetic anticipation in adult-onset idiopathic dystonia," *Neurology*, 47(1):215-219 (1996).
David, G. et al., "Cloning of the SCA7 gene reveals a highly unstable CAG repeat expansion," *Nature Genetics*, 17(1):65-70 (Sep. 1997).
David et al., "The Gene for Autosomal Dominant Cerebellar Ataxia Type II Is Located in a 5-cM Region in 3p12-p13: Genetic and Physical Mapping of the SCA7 Locus," *Am. J. Hum. Genet.*, 59, 1328-1336 (1996).
Engstrom et al., "Anticipation in unipolar affective disorder," *J. Affect. Dis.*, 35(1-2):31-40 (1995).
Fu et al., "An unstable triplet repeat in a gene related to myotonic muscular dystrophy," *Science*, 255(5049):1256-1258 (1992).
Gizatullin et al., "*H. sapiens* DNA Not] jumping clone J32Z180D," Genbank Accession No.: X95831.
Gouw et al., "Retinal degeneration characterizes a spinocerebellar ataxia mapping to chromosome 3p," *Nature Genetics*, 10, 89-93 (1995).
Harley et al., "Expansion of an unstable DNA region and phenotypic variation in myotonic dystrophy," *Nature*, 355(6360):545-546 (1992).
Higgins et al., "Evidence for a new spinocerebellar ataxia locus," *Movement Disorders*, 12(3):412-417 (1997).
Hillier et al., "Soares adult brain N2b5HB55Y *Homo sapiens* cDNA clone. mRNA sequence," Genbank Accession No.: H40285.
Hillier et al., "Soares adult brain N2b5HB55Y *Homo sapiens* cDNA clone, mRNA sequence," Genbank Accession No.: H40290.
Hillier et al., "Soares adult brain N2b5HB55Y *Homo sapines* cDNA clone, mRNA sequence," Genbank Accession No.: H41756.

(Continued)

*Primary Examiner*—Young J. Kim
(74) *Attorney, Agent, or Firm*—Mueting Raasch & Gebhardt, P.A.

(57) ABSTRACT

The present invention provides diagnostic methods of identifying individuals at risk and not at risk of developing spinocerebellar ataxia type 7. The present invention also provides for methods for identifying expanded repeats, and the DNA flanking the expanded repeats, from genomic DNA.

8 Claims, 10 Drawing Sheets

OTHER PUBLICATIONS

*Homo sapiens* mRNA for spinocerebellar ataxia 7, Genbank Accession No. AJ000517 (available on or before Dec. 6, 2000).

*Homo sapiens* spinocerebellar ataxia 7 (SCA7) gene, partial cds, Genbank Accession No. AF020276 (available on or before Dec. 6, 2000).

Huntington's Disease Collaborative Research Group, The, "A novel gene containing a trinucleotide repeat that is expanded and unstable on Huntington's disease chromosomes," *Cell*, 72(6):971-983 (1993).

Imbert et al., "Cloning of the gene of spinocerebellar ataxia 2 reveals a locus with high sensitivity to expanded CAG/glutamine repeats," *Nature Genetics*, 14(3):285-291 (1996).

Imbert et al., "Towards cloning of the genes for two polyglutamine expansion diseases SCA3 and SCA7," *American Journal of Human Genetics*, 59(4 Suppl.), Abstract No. 1528, A264 (1996).

Kawaguchi et al., "CAG expansions in a novel gene for Machado-Joseph disease at chromosome 14q32.1," *Nature Genetics*, 8(3):221-228 (1994).

Kohler et al., "Derivation of specific antibody-producing tissue culture and tumor lines by cell fusion," *Eur. J. Immunol.*, 6, 511-519 (1976).

Koide et al., "Unstable expansion of CAG repeat in hereditary dentatorubral-pallidoluysian atrophy (DRPLA)," *Nature Genetics*, 6(1):9-13 (1994).

Koob, et al., "Rapid cloning of expanded trinucleotide repeat sequences from genomic DNA," *Nature Genetics*, 18(1):72-75 (Jan. 1998).

Kremer et al., "Mapping of DNA instability at the fragile X to a trinucleotide repeat sequence p(CCG)n," *Science*, 252(5013):1711-1714 (1991).

Kunkel et al., "Rapid and Efficient Site-Specific Mutagenesis without Phenotypic Selection," *Methods in Enzymology*, 154, 367-382 (1987).

La Spada et al., "Androgen receptor gene mutations in X-linked spinal and bulbar muscular atrophy," *Nature*, 352(6330):77-79 (1991).

Levitan, M., "Human Chromosomes, Banding Methods", in *Textbook of Human Genetics*, third edition, Oxford University Press, New York, pp. 32-35 (1988).

Lindblad t et al., "GAG repeat expansions in SCA," *American Journal of Human Genetics*, 59(4 Suppl.), Abstract No. 1557, A269 (1996).

Lindblad et al., "Growing triplet repeats," *Nature Genetics*, 7, 124 (1994).

Lindblad et al., "An Expanded CAG Repeat Sequence in Spinocerebellar Ataxia Type 7," *Genome Research*, 6, 965-971 (1996).

Mahadevan et al., "Myotonic Dystrophy Mutation: An unstable CTG repeat in the 3' untranslated region of the gene," *Science*, 255(5049):1253-1255 (1992).

Maraganore et al., "Anticipation in familial Parkinson's disease: A reanalysis of 13 United Kingdom kindreds," *Neurology*. 47. 1512-1517 (1996).

Marx, "Putting the Human Genome on the Map," *Science*, 229, 150-151 (1985).

Maxam et al., "Sequencing End-Labeled DNA with Base-Specific Chemical Cleavages," *Methods in Enzymology*, 65, 499-560 (1980).

McInnis et al., "Anticipation in bipolar affective disorder," *Am. J. Hum. Genet.*, 53(2):385-390 (1993).

Messing et al., "A system for shotgun DNA sequencing," *Nucl. Acids Res.*, 9, 309 (1981).

O'Donovan et al., "Expanded CAG repeats in schizophrenia and bipolar disorder," *Nature Genetics*, 10(4):380-381 (1995).

Orr, principal investigator, "Hereditary Ataxia—Molecular Genetics & Pathophysiology," Abstract, Grant No. 5P01NS33718-04 in FY 1998, sponsored by the National Institute of Neurological Disorders and Stroke, National Institutes of Health (Available on-line on or before Jan. 22, 2001).

Orr, principal investigator, "Mapping/Isolation of a Novel Spinocereb," Abstract, Grant No. 5P01NS33718-040003 in FY 1998, sponsored by the National Institute of Neurological Disorders and Stroke, National Institutes of Health (Available on-line on or before Jan. 22, 2001).

Orr et al., "Expansion of an unstable trinucleotide CAG repeat in spinocerebellar ataxia type 1," *Nature Genetics*, 4(3):221-226 (1993).

Oruc et al., "CAG Repeat Expansions in Bipolar and Unipolar Disorders," *Am. J. Hum. Genet.*, 60, 730-732 (1997).

Ostrander et al., "Construction of small-insert genomic DNA libraries highly enriched for microsatellite repeat sequences," *Proc. Natl. Acad. Sci. USA*, 89, 3419-3423 (1992).

Petronis et al., "Direct detection of expanded trinucleotide repeats using PCR and DNA hybridization techniques," *Am. J. Med. Genet.*, 67(1):85-91 (1996).

Plante-Bordeneuve et al., "A clinical and genetic study of familial cases of Parkinson's disease," *J. Neurol. Sci.*, 133(1-2):164-172 (1995).

Pulst et al., "Moderate expansion of a normally biallelic trinucleotide repeat in spinocerebellar ataxia type 2," *Nature Genetics*, 14(3):269-276 (1996).

Ranum et al., "Spinocerebellar Ataxia Type 1 and Machado-Joseph Disease: Incidence of CAG Expansions among Adult-Onset Ataxia Patients from 311 Families with Dominant, Recessive, or Sporadic Ataxia," *Am. J. Hum. Genet.*, 57, 603-608 (1995).

Saiki et al., "Enzymatic Amplification of β-Globin Genomic Sequences and Restriction Site Analysis for Diagnosis of Sickle Cell Anemia," *Science*, 230, 1350-1354 (1985).

Sambrook et al., *Molecular Cloning: A Laboratory Manual*, Cold Spring Harbor Laboratory, New York, cover page and table of contents, and pp. 11.2-11.4 (1989).

Sanpei et al., "Identification of the spinocerebellar ataxia type 2 gene using a direct identification of repeat expansion and cloning technique, DIRECT," *Nature Genetics*, 14(3):277-284 (1996).

Schalling et al., "Direct detection of novel expanded trinucleotide repeats in the human genome," *Nature Genetics*, 4, 135-139 (1993).

Scharf et al.. "Direct Cloning and Sequence Analysis of Enzymatically Amplified Genomic Sequences," *Science*, 233, 1076-1078 (1986).

Schuler et al., "A Gene Map of the Human Genome," *Science*, 274, 540-546 (1996).

Verkerk et al., "Identification of a gene (FMR-1) containing a CCG repeat coincident with a breakpoint cluster region exhibiting length variation in fragile X syndrome," *Cell*, 65(5):905-914 (1991).

Vieira et al., "Production of Single-Stranded Plasmid DNA," *Meth. in Enzymology*, 153, 3-11 (1987).

Warren, "The Expanding World of Trinucleotide Repeats," *Science*, 271, 1374-1375 (1996).

Zhuchenko et al., "Autosomal dominant cerebellar ataxia (SCA6) associated with small polyglutamine expansions in the alpha 1A-voltage-dependent calcium channel," *Nature Genetics*, 15(1):62-69 (1997).

* cited by examiner

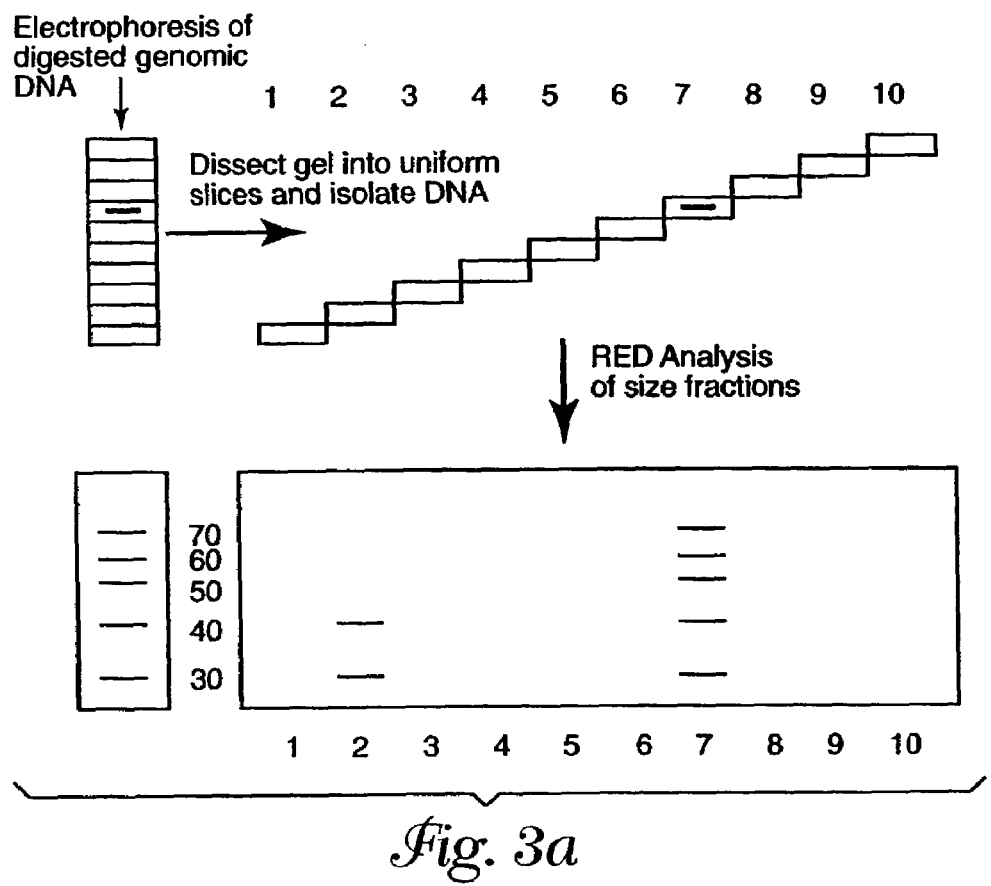
*Fig. 3a*
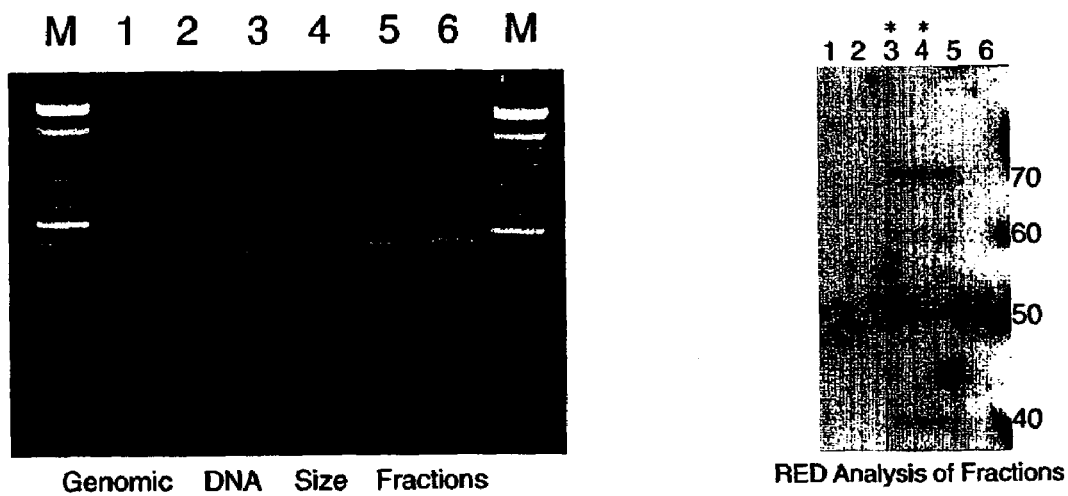
*Fig. 3b*  *Fig. 3c*

```
CAAGCAGAAAGGGGGCTGCAAAGCTGCCTGCCTAGGGCTACGTTTCCTGGCAAAACTTCC   60
GAAAGCCATTTCTCCAAAAGAAGGTCTAGAAGAGGAGGAGGAGGAGGAGAAGGAGGAGGA  120
GGAGGAGGAGCAGCAGCAGCAGCAGCAGCAGCAGCAGCAGCAGCAGCAGCAGCAGCAGCA  180
GCATGAAAGAGCCCCACTTGGAAGGCGGTTTGGATTTTATTTGTGTGTTTTGTGGATTCT  240
TTTTATTTTGCTTTACAAATGCATCTTACACCAAACTCATCTGGCATTAAAAATGAATTC  300
```

Fig. 5d

*Fig. 7a*

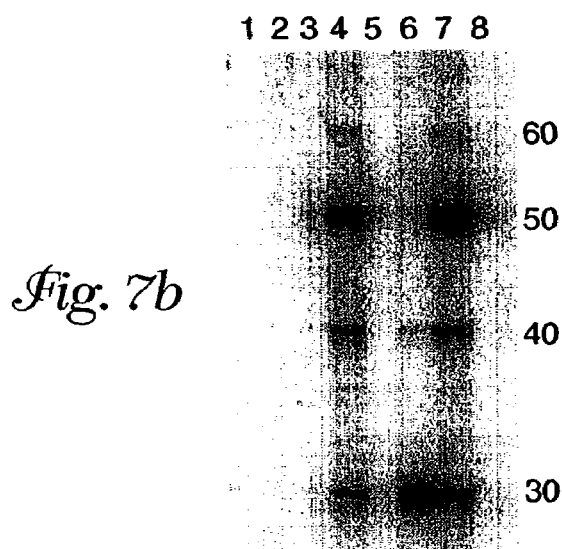

*Fig. 7b*

```
CGACTCTTTCCCCCTTTTTTTTGTTACATTGTAGGAGCGGAAAGAATGTCGGAGCGGGCC    60
GCGGATGACGTCAGGGGGGAGCCGCGCCGCGCGGCGGCGGCGGCGGGCGGAGCAGCGGCC   120
GCCCGGCAGCAGCAGCAGCAGCAGCAGCAGCAGCAGCAGCAGCAGCAGCAGCAGCAGCAG   180
CAGCAGCAGCAGCAGCAGCAGCAGCAGCAGCAGCAGCAGCAGCAGCAGCAGCAGCAGCAG   240
CAGCAGCAGCAGCAGCAGCAGCAGCAGCAGCAGCAGCAGCAGCCGCCGCCTCCGCAG      300
CCCCAGCGGCAGCAGCACCCGCCACCGCCGCCACGGCGCACACGGCCGGAGGACGGCGGG   360
CCCGGCGCCGCCTCCACCTCGGCCGCCGCAATGGCGACGGTCGGGGAGCGCAGGCCTCTG   420
CCCAGTCCTGAAGTGATGCTGGGACAGTCGTGGAATCTGTGGGTTGAGGCTTCCAAA
```

*Fig. 7c*

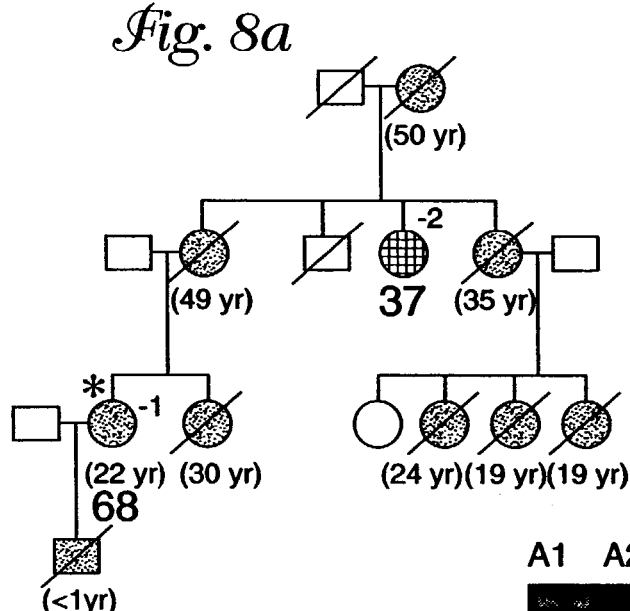
Fig. 8a
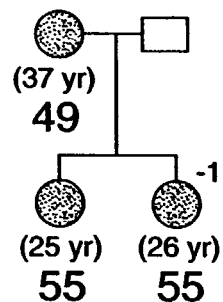
Fig. 8b
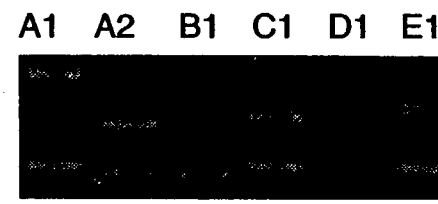
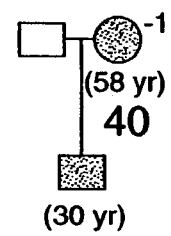
Fig. 8c
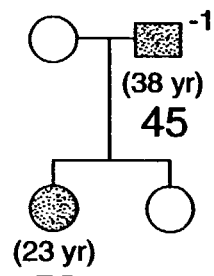
Fig. 8d
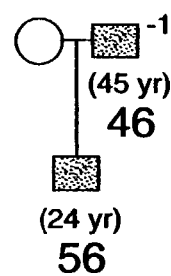
Fig. 8e

SCA7 GENE AND METHODS OF USE

This is a Continuation Application of U.S. patent application Ser. No. 09/684,843, filed on Oct. 6, 2000 now U.S. Pat. No. 6,514,755, which is a Division of U.S. patent application Ser. No. 09/135,994, filed on Aug. 18, 1998 now U.S. Pat. No. 6,280,938, which in turn claims the benefit of U.S. Provisional Application Ser. No. 60/056,170, filed on Aug. 19, 1997, which are all incorporated herein by reference.

STATEMENT OF GOVERNMENT RIGHTS

The present invention was made with government support under Grant No. 5PO1-NS33718-03, awarded by the National Institutes of Health. The Government has certain rights in this invention.

BACKGROUND OF THE INVENTION

Trinucleotide repeat expansions have been shown to be the mutational mechanism responsible for a growing number of diseases, including Fragile X mental retardation, spinobulbar muscular atrophy, myotonic dystrophy (DM), Huntington disease (HD), spinocerebellar ataxia (SCA) types 1,2,3 and 6, dentatorubral pallidoluysian atrophy and Friedreich's ataxia. A hallmark for most of these diseases is the presence of anticipation, or a decrease in the age of onset and increase in disease severity in consecutive generations due to the tendency for the unstable trinucleotide repeat tract to lengthen when passed from one generation to the next (Warren, S. T. *Science*, 271, 1374–1375 (1996)).

In 1993, Schalling et al. (*Nature Genetics*, 4, 135–139 (1993)) developed the repeat expansion detection (RED) assay. RED is an elegant technique that detects potentially pathological trinucleotide repeat expansions without prior knowledge of chromosomal location or flanking DNA sequence. Human genomic DNA is used as a template for a two-step ligation cycling process that generates sequence specific [$(CAG)_n$, $(CGG)_n$, etc.] oligonucleotide multimers when expanded trinucleotide sequences are present in the genome. The assay was originally developed to detect very large trinucleotide repeat expansions present in genomic DNA from patients with Myotonic Dystrophy (DM) and Fragile X syndrome (up to 2,000 repeats). Since that time, Lindblad et al. have modified the procedure to detect smaller trinucleotide repeats in the size range (40–100 CAG repeats) pathologic for SCA1, SCA3, HD, and SBMA (Lindblad, K., et al., *Nature Genetics* 7, 124 (1994), Lindblad, K. et al., *Genome Research*, 6, 965–971 (1996)).

This modified assay has been used to establish correlations that suggest the involvement of CAG expansions in diseases such as SCA7 (Lindblad, K. et al., *Genome Research*, 6, 965–971 (1996)), bipolar affective disorder (Oruc, L. et al., *Am J Hum Genet.*, 60, 732–735 (1997)) and schizophrenia (Maraganore, D. M., et al., *Neurology*, 47, (1996)).

The spinocerebellar ataxias (SCAs) are progressive degenerative neurological diseases of the nervous system characterized by a progressive degeneration of neurons of the cerebellar cortex. Degeneration is also seen in the deep cerebellar nuclei, brain stem, and spinal cord. Clinically, affected individuals suffer from severe ataxia and dysarthria, as well as from variable degrees of motor disturbance and neuropathy. The disease usually results in complete disability and eventually in death 10 to 30 years after onset of symptoms. The genes for SCA types 1, 2, 3 and 6 have been identified. All contain CAG DNA repeats that cause the disease when the repeat region is expanded. Little is known how CAG repeat expansion and elongation of polyglutamine tracts relate to neurodegeneration. The identification of the SCA7 gene would provide an opportunity to study this phenomenon in a new protein system.

The significance of identifying ataxia genes provides an improved method for diagnosis of individuals with the disease and increases the possibility of prenatal/presymptomatic diagnosis or better classification of ataxias. Most of the genes associated with repeat expansions in the coding region including the other SCA genes now identified, show no homology to known genes.

SUMMARY OF THE INVENTION

The present invention relates to methods for identifying individuals at risk and individuals not at risk for developing spinocerebellar ataxia type 7. These methods include the step of analyzing the CAG repeat region of a spinocerebellar ataxia type 7 gene wherein individuals at risk for developing spinocerebellar ataxia type 7 typically have at least about 30, more typically at least about 37 and even more typically at least about 38 CAG repeats. A person not at risk typically has less than about 19, more typically less than about 15, and even more typically less than about 5 CAG repeats. The methods can include the steps of performing a polymerase chain reaction with oligonucleotide primers capable of amplifying the CAG repeat region located within the spinocerebellar ataxia type 7 gene, and detecting amplified DNA fragments containing the CAG repeat region. The oligonucleotide primers can be selected from the nucleotide region of SEQ ID NO:9 and from the region of SEQ ID NO:10. Preferred oligonucleotide primers are SEQ ID NO:5 and SEQ ID NO:6.

The methods for identifying individuals at risk for developing spinocerebellar ataxia type 7 can also include detecting the presence of a DNA molecule containing a CAG repeat region of the SCA7 gene by probing genomic DNA digested with a restriction endonuclease and probing the DNA fragments under hybridizing conditions with a detectably labeled gene probe so as to detect a nucleic acid molecule containing a CAG repeat region of an isolated SCA7 gene.

The present invention provides isolated nucleic acids encoding the human SCA7 protein and portions thereof, and isolated proteins and portions thereof encoded from the nucleic acid. The invention also relates to isolated DNA fragments, vectors and isolated recombinant vectors containing the nucleic acids of this invention, oligonucleotide probes and primers that hybridize the SCA7 nucleic acid, host cells transformed or transfected with SCA7 or fragments thereof, compositions containing antibodies that specifically bind to polypeptides encoded by all or part of the SCA7 nucleic acid, a method for detecting the SCA7 disorder including using a biological sample to form an antibody-antigen complex, and to model systems that express the SCA7 protein.

The present invention provides for a kit for detecting whether or not an individual is at risk for developing spinocerebellar ataxia type 7. One preferred kit includes oligonucleotides selected from the nucleotide region of SEQ ID NO:9 and from the region of SEQ ID NO:10.

In another aspect of this invention, the invention relates to a procedure for rapidly identifying and isolating expanded repeats and the corresponding flanking nucleotide sequence directly from small amounts of genomic DNA using a process of Repeat Analysis, Pooled Isolation, and Detection of individual clones containing expanded repeats (RAPID cloning). The method includes the steps of fractionating a population of DNA fragments and detecting the fraction that contains an expanded repeat, cloning the DNA fragments contained in the fraction of DNA that contains an expanded repeat, and identifying the clones that contain the expanded repeat. The fractionation step can include digesting genomic DNA with a restriction enzyme to obtain DNA fragments, resolving the DNA fragments by gel electrophoresis, dividing into fractions on the basis of size, and detecting the presence of an expanded repeat in each size fraction. The nucleotide sequence flanking the expanded repeat can then be determined and used to design a PCR assay to determine if a particular repeat cosegregates with a given disease.

The invention also relates to an improvement of the repeat expansion detection assay where the rate of temperature change from the denaturation temperature is decreased and wherein the ligation buffer contains formamide. Preferably, the rate of temperature change from the denaturation temperature is decreased to 2 seconds per degree and the ligation buffer contains 4% formamide.

BRIEF DESCRIPTION OF THE FIGURES

FIG. 3 Two-dimensional RED (2D-RED) analysis. A: Schematic overview of the 2D-RED procedure. Genomic DNA is digested with a restriction enzyme and size-separated on an agarose gel. The lane containing the DNA is excised and uniformly cut every 2 mm along its length using a gel-slicing device. Each slice is placed in a separate eppendorf tube, the agarose is digested, and the DNA is precipitated and resuspended in a small volume of buffer. RED analysis is then performed on individual size fractions. In the example shown schematically, a genomic DNA sample that generates a RED70 product (left) is resolved by 2D-RED into separate RED40 and RED70 size fractions (right). B: Genomic DNA from an individual with a known SCA3 expansion was digested with MboI and size-fractionated. The size distribution of the critical fractions as measured by running a portion on an agarose gel is shown. C: RED analysis of the size fractions shown in panel "B". Fractions 3 and 4 generate the RED70 product expected for the expanded SCA3 allele present in the original genomic sample.

FIG. 7 RAPID cloning of the SCA7 expanded CAG repeat. A: 2D-RED analysis of EcoRI-digested genomic DNA isolated from an individual with an autosomal dominant ataxia with rentinopathy (individual A1, FIG. 8). The genomic DNA size-fraction containing the CAG expansion (indicated by *) was cloned into a lambda vector. The resulting library was amplified in pools that were converted en masse into plasmid library pools. B: RED analysis of CTG-enriched clone pools derived from a RED-positive primary clone pool. Each pool contains DNA from 36 individual clones. RED analysis of plasmid DNA from the individual clones in pool 4 identified two clones containing the expanded CAG repeat. C: Nucleotide sequence (SEQ ID NO:1) of the gcnomic DNA flanking the SCA7 expansion in clone 4-2. The CAG expansion is underlined.

FIG. 8 PCR analysis of the SCA7 CAG alleles in kindreds diagnosed with autosomal dominant ataxia with retinopathy. The estimated age of onset (in parentheses) and number of CAG repeats in the SCA7 expansion is indicated numerically in each kindred. The individual from whom the expanded CAG was isolated is starred (A1). Agarose gel analysis of the PCR products generated from genomic DNA of the indicated individuals is shown in the inset. An expanded allele was present only in affected or at-risk individuals, and the size of the expansion is inversely proportional to the age of onset.

DETAILED DESCRIPTION OF THE PREFERRED EMBODIMENTS

Figure 1:
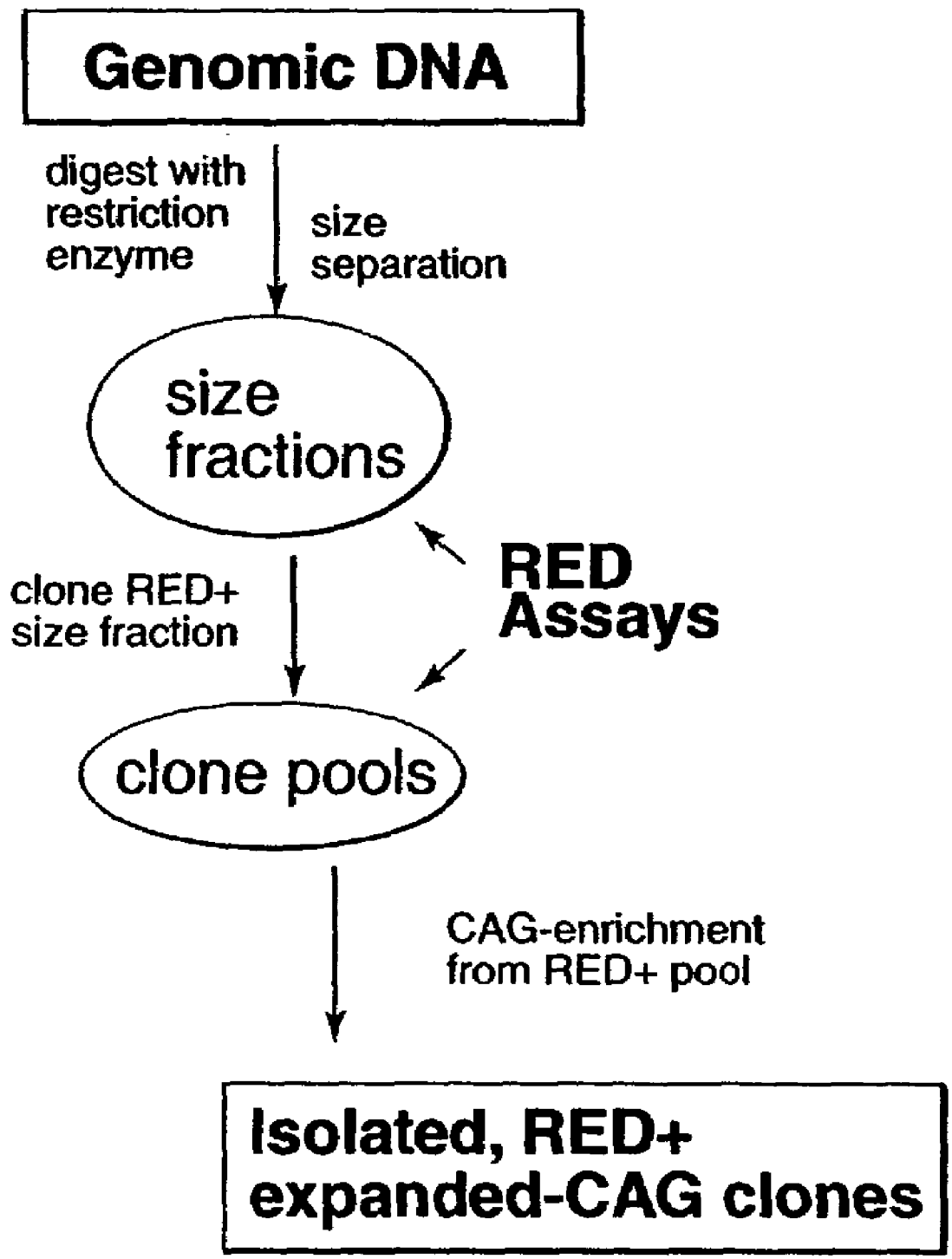
FIG. 1 Schematic overview of RAPID cloning of expanded trinucleotide repeats from genomic DNA and cDNA. In general, the Repeat Expansion Detection (RED) assay is used to follow an expanded trinucleotide repeat present in either genomic DNA or cDNA through a series of enrichment steps until a single, purified clone is obtained. Genomic DNA is digested with a restriction enzyme, the fragments are size-fractionated with agarose gel electrophoresis, and RED analysis is performed on the size fractions to determine which contains an expanded CAG repeat (FIG. 3). The RED positive fraction is cloned, DNA from clone pools consisting of approximately $5 \times 10^4$ clones each are assayed, and a RED positive clone pool is subjected to a post-cloning CAG-enrichment procedure (FIG. 5). Clones from the enriched library are then assayed either individually or in small pools of approximately 20 clones each to determine which clones contain the CAG-expansion.

The hereditary ataxias are a complex group of neurodegenerative disorders all characterized by varying abnormalities of balance attributed to dysfunction or pathology of the cerebellum and cerebellar pathways. In many of these disorders, dysfunction or structural abnormalities extend beyond the cerebellum and may involve basal ganglia function, oculo-motor disorders and neuropathy. Substantial efforts have been made to determine the genetic bases of the spinocerebellar ataxias (SCAs). SCA genes have been identified on different chromosomes and have different conserved sequences. While all contain CAG DNA repeats that are associated with disease when the repeat is expanded, the underlying mechanism leading to neurodegeneration is unknown. Moreover, the high phenotypic variability within single SCA pedigrees has made clinical classification of different forms of ataxia difficult.

The gene for SCA type 7 has been identified and isolated. The isolation of the SCA7 gene allows the easy diagnosis of one type of the spinocerebellar ataxias. Diagnosis can be the presymptomatic identification of individuals at risk of ataxia, including the identification of individuals where there is no family history of the disease.

In one aspect of this invention, a method for identifying genes with expanded repeats is provided. As used herein, "expanded repeat" or "repeat expansion" refers to a single short repeating unit of nucleotides. The repeating unit can typically include between 2 and 8 nucleotides. These repeats can present in the coding sequence of genes that encode polypeptides that function properly. In some individuals the number of repeats increases or expands in number and translation of the gene containing an expanded repeat can result in a polypeptide than causes disease. A repeat is considered to be an expanded repeat when the number of consecutive repeats is associated with disease. An expanded repeat includes repeats of 2 nucleotides (dinucleotide repeat), 3 nucleotides (trinucleotide repeat), etc., up to and including repeats of 8 nucleotides, for example.

Any gene containing an expanded repeat can be identified by this method. Preferably, a gene identified by this method will contain a trinucleotide repeat, including for instance genes for SCA types 1, 2, 3, 6 and 7. Utilization of different oligonucleotides allows any of the 10 possible trinucleotide repeats to be detected (Lindblad, K., et al., Nature Genetics 7, 124 (1994)). Preferably, the CAG repeat is identified. Preferably, the CAG repeat is present in the SCA7 gene or in the gene comprising the nucleotides of SEQ ID NO:3. This method first optimizes a repeat expansion detection assay and provides methods for enriching and isolating DNA containing expanded CAG repeats and flanking DNA. Preferably, the number of CAG repeats is greater than 20. More preferably, the number of CAG repeats is greater than 30.

One method to detect expanded repeats is the repeat expansion detection (RED) assay. RED analysis has been performed on a several of these patient populations and has led to reports of correlations between trinucleotide expansions and disease. However, RED analysis with defined genomic DNA control templates yields inconsistent results and typically does not correlate with size of the largest known CAG expansion in the genomic sample. Another limitation of RED analysis has been that although it can detect novel trinucleotide expansions, RED alone cannot directly determine if an expanded repeat causes disease or is merely one of a number of background repeat expansions found in the general population. Consequently, the role of an expanded trinucleotide repeat as a possible pathogenic mutation in a disease kindred must be conclusively confirmed. This requires the isolation of the expansions present in these populations and detailed PCR analysis to assess whether of not the expanded trinucleotide repeat cosegregates with the disease.

A. Trinucleotide Repeat Expansions and Method of Diagnosis

The identification of an improved method to identify trinucleotide repeat expansions associated with a disease allows for improved diagnosis of the disease. Thus, the present invention relates to methods of diagnosing individuals at risk of developing diseases that are caused by a trinucleotide repeat expansion. The invention also relates to methods of diagnosing individuals not at risk. These diagnostic methods can be used to identify individuals at risk of developing spinocerebellar ataxia type 1, 2, 3, 6 or 7 by analyzing the trinucleotide repeat region of a gene. Preferably, the CAG repeat is identified. Preferably, the CAG repeat is present in the SCA7 gene. The SCA7 gene of an individual not at risk of developing spinocerebellar ataxia type 7 typically contains less than about 19, more typically less than about 15, and even more typically less than about 5 CAG repeats. The SCA7 gene of an individual at risk of developing spinocerebellar ataxia type 7 typically contains at least about 30, more typically at least about 37 and even more typically at least about 38 CAG repeats.

These diagnostic methods can involve any known method for detecting a specific fragment of DNA. These methods can include direct detection of the DNA or indirect through detection through the detection of RNA or proteins, for example. For example, RED analysis can be used. Alternatively, Southern or Northern blotting hybridization techniques using labeled probes can be used. PCR techniques can be used with novel primers that amplify the CAG repeating region of a gene containing a trinucleotide repeat expansion. Nucleic acid sequencing can also be used as a direct method of determining the number of trinucleotide repeats.

As used herein, "hybridizes," "hybridizing" and "hybridization" means that the oligonucleotide forms a noncovalent interaction with the stringency target nucleic acid molecule under standard conditions. The hybridizing oligonucleotide may contain nonhybridizing nucleotides that do not interfere with forming the noncovalent interaction, e.g., a restriction enzyme recognition site to facilitate cloning.

The gene for SCA7 contains a highly polymorphic CAG repeat that is located within a 1.86 kb fragment produced by digestion of the candidate region with the restriction enzyme, EcoRI. The CAG repeat region preferably lies within the coding region and codes for polyglutamine. This region of CAG repeating sequences is unstable and expanded in individuals with SCA7. PCR analysis of the $(CAG)_n$ repeat, for example, demonstrates a correlation between the size of the repeat expansion and the age-at-onset of SCA7 and severity of the disorder. That is, individuals with more repeat units (or longer repeat tracts) tend to have both an early age of onset and a more severe disease course. These results demonstrate that SCA7, like hereditary ataxia associated with SCA1, fragile X syndrome, myotonic dystrophy, X-linked spinobulbar muscular atrophy, and Huntington disease, displays a mutational mechanism involving expansion of an unstable trinucleotide repeat.

In one embodiment of the present invention, DNA probes can be used for identifying DNA segments of the affected allele of the SCA7 gene. DNA probes are segments of labeled, single-stranded DNA which will hybridize, or non-covalently bind, with complementary single-stranded DNA derived from the gene sought to be identified. The probe can be labeled with any suitable label known to those skilled in the art, including radioactive and nonradioactive labels. Typical radioactive labels include $^{32}$P, $^{125}$I, $^{35}$S, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe may also be labeled at both ends with different types of labels for ease of separation, as, for example, by using an isotopic label at one end and a biotin label at the other end.

The present invention relates to a method for detecting the presence of DNA molecules containing a CAG repeat region where a sample of genomic DNA is digested with a restriction endonuclease, and probing the resulting DNA fragments with an oligonucleotide probe. Using DNA probe analysis, the target DNA can be derived by the enzymatic digestion, fractionation, and denaturation of genomic DNA to yield a complex mixture incorporating the DNA from many different genes, including DNA from the short arm of chromosome 3, which includes the SCA7 locus. A specific DNA gene probe will hybridize only with DNA derived from its target gene or gene fragment, and the resultant complex can be isolated and identified by techniques known in the art. In one embodiment, the method involves digesting genomic DNA with a restriction endonuclease to obtain DNA fragments, probing the fragments under hybridizing conditions with a detectably labeled gene probe, which hybridizes to a nucleic acid molecule containing a CAG repeat region of an isolated SCA7 gene having at least about 11 nucleotides, detecting probe DNA which has hybridized to the DNA fragments, and analyzing the DNA fragments for a CAG repeat region characteristic of the normal or affected forms of the SCA7 gene.

The probes are oligonucleotides, either synthetic or naturally occurring, capable of hybridizing to the region of the DNA sequence flanking the CAG repeating trinucleotides and optionally hybridizing to the DNA sequence encoding the CAG repeat. Preferably, the probes hybridize to the the SCA7 locus of the short arm of chromosome 3. The probe includes a nucleotide sequence substantially complementary to a portion of a strand of an affected or a normal allele of a fragment (preferably a 1.86 kb EcoRI fragment) of an SCA7 gene having a $(CAG)_N$ region. The probe sequence has at least about 11 nucleotides, preferably at least 15 nucleotides and no more than about 35 nucleotides. The probes are chosen such that the nucleotide sequence is substantially complementary to a portion of a strand of an affected or a normal allele within about 1000 nucleotides 5' of the $(CAG)_N$ region, including directly adjacent to the $(CAG)_N$ region. Alternatively, the probes are chosen such that nucleotide sequence is substantially complementary to a portion of a strand of an affected or a normal allele within about 800 nucleotides 3' of the $(CAG)_N$ region, including directly adjacent to the $(CAG)_n$ region. The probes can also comprise at least 15 nucleotides from SEQ ID NO:9, SEQ ID NO:10, SEQ ID NO:13 or SEQ ID NO:14.

In general, for detecting the presence of a DNA sequence located within the SCA7 gene, the genomic DNA is digested with a restriction endonuclease to obtain DNA fragments. The source of genomic DNA to be tested can be any biological specimen that contains DNA. Examples include specimens of blood, semen, vaginal swabs, tissue, hair, and body fluids. The restriction endonuclease can be any that will cut the genomic DNA into fragments of double-stranded DNA having a particular nucleotide sequence. The specificities of numerous endonucleases are well known and can be found in a variety of publications, e.g. Sambrook et al.; *Molecular Cloning: A Laboratory Manual*; Cold Spring Harbor Laboratory: New York (1989). Preferred restriction endonuclease enzymes include EcoRI, TaqI, and BstNI. EcoRI is particularly preferred.

Diagnosis of the disease can alternatively involve the use of the polymerase chain reaction sequence amplification method (PCR) using novel primers. U.S. Pat. No. 4,683,195 (Mullis et al., issued Jul. 28, 1987) describes a process for amplifying, detecting and/or cloning nucleic acid sequences. This method involves treating extracted DNA to form single-stranded complementary strands, treating the separate complementary strands of DNA with a molar excess of two oligonucleotide primers, extending the primers to form complementary extension products that act as templates for synthesizing the desired nucleic acid molecule, detecting the amplified DNA molecule, and analyzing the amplified molecule for a CAG repeat region characteristic of the SCA7 disorder. More specifically, the method steps of treating the DNA with primers and extending the primers include the steps of: adding a pair of oligonucleotide primers, wherein one primer of the pair is substantially complementary to part of the sequence in the sense strand and the other primer of each pair is substantially complementary to a different part of the same sequence in the complementary antisense strand; annealing the paired primers to the complementary molecule; simultaneously extending the annealed primers from a 3' terminus of each primer to synthesize an extension product complementary to the strands annealed to each primer wherein said extension products after separation from the complement serve as templates for the synthesis of an extension product for the other primer of each pair; and separating said extension products from said templates to produce single-stranded molecules. Variations of the method are described in U.S. Pat. No. 4,683,194 (Saiki et al., issued Jul. 28, 1987). The polymerase chain reaction sequence amplification method is also described by Saiki et al., *Science*, 230, 1350–1354 (1985) and Scharf et al., *Science*, 233, 1076–1078 (1986).

As used herein, the term "amplified DNA molecule" and "amplified DNA fragment" refers to DNA molecules that are copies of a portion of DNA and its complementary sequence. The copies correspond in nucleotide sequence to the original DNA sequence and its complementary sequence. The term "complement" and "complementary" as used herein, refers to a DNA sequence that is complementary (having greater than 65% homology) to a specified DNA sequence. The term "primer pair", as used herein, means a set of primers including a 5' upstream primer that hybridizes with the 5' end of the DNA molecule to be amplified and a 3' downstream primer that hybridizes with the complement of the 3' end of the molecule to be amplified.

The primers are oligonucleotides, either synthetic or naturally occurring, capable of acting as a point of initiating synthesis of a product complementary to the region of the DNA sequence containing the CAG repeating trinucleotides of the SCA7 locus of the short arm of chromosome 3. The primer includes a nucleotide sequence substantially complementary to a portion of a strand of an affected or a normal allele of a fragment (preferably a 1.86 kb EcoRI fragment) of an SCA7 gene having a $(CAG)_n$ region. The primer sequence has at least about 11 nucleotides, and preferably, at least about 16 nucleotides and no more than about 35 nucleotides. The primers are chosen such that they produce a primed product of about 70–350 base pairs, preferably about 100–300 base pairs. More preferably, the primers are chosen such that nucleotide sequence is substantially complementary to a portion of a strand of an affected or a normal allele within about 150 nucleotides on either side of the $(CAG)_n$ region, including directly adjacent to the $(CAG)_n$ region.

The invention discloses conserved regions flanking the CAG repeat region of SCA7. Oligonucleotides suitable for polymerase chain reaction amplification can be selected from the regions flanking the CAG repeat region both 5' and 3' to the CAG repeat region. The regions of the SCA7 gene from which oligonucleotide primers can be selected are from the nucleotides of SEQ ID NO:9 and SEQ ID NO:10. Preferred primers are SEQ ID NO:5 and SEQ ID NO:6. This primer set successfully amplifies the CAG repeat units of interest using PCR technology. These oligonucleotides are useful for amplifying the CAG repeat region from the SCA7 gene from DNA taken from an individual suspected of having spinocerebellar ataxia. Oligonucleotide primers can also be selected from the nucleotides of SEQ ID NO:13 and SEQ ID NO:14. The amplified fragments can be run on a gel to detect the length of the CAG repeat region. Individuals at risk for developing spinocerebellar ataxia type 7 typically have at least about 30, more typically at least about 37 and even more typically at least about 38 CAG repeats. A person not at risk typically has less than about 19, more typically less than about 15, and even more typically less than about 5 CAG repeats. Alternatively, the primer pair can be used in various known techniques to sequence the SCA7 gene.

The invention also relates to a kit for detecting whether or not an individual is at risk for developing the disease associated with an expanded repeat. The method used in the kit for detecting whether or not an individual is at risk for developing the disease associated with an expanded repeat includes all methods for detecting an extended repeat disclosed herein. Preferably, the expanded repeat detected is CAG. Preferably, the CAG repeat is present in the SCA7 gene.

As stated previously, other methods of diagnosis can be used as well. They can be based on the isolation and identification of the repeat region of genomic DNA (CAG repeat region), cDNA (CAG repeat region), mRNA (CAG repeat region), and protein products (glutamine repeat region). These include, for example, using a variety of electrophoresis techniques to detect slight changes in the nucleotide sequence of the SCA7 gene. Further nonlimiting examples include denaturing gradient electrophoresis, single strand conformational polymorphism gels, and nondenaturing gel electrophoresis techniques.

The mapping and cloning of the SCA7 gene allows the definitive diagnosis of one type of the dominantly inherited ataxias using a simple blood test. This represents the first step towards an unequivocal molecular classification of the dominant ataxias. A simple and reliable classification system for the ataxias is important because the clinical symptoms overlap extensively between the SCA7 and the non-SCA7 forms of the disease. Furthermore, a molecular test for the only known SCA7 mutation permits presymptomatic diagnosis of disease in known SCA7 families and allows for the identification of sporadic or isolated CAG repeat expansions where there is no family history of the disease. Thus, the present invention can be used in family counseling, planning medical treatment, and in standard work-ups of patients with ataxia of unknown etiology.

B. Identification of Expanded Repeats from Genomic DNA

One aspect of this invention relates to an improved method of performing RED analysis to evaluate the presence and size of expanded repeats in a DNA sample.

Another aspect of this invention relates to a method (referred to as 2D-RED) of identifying a genomic size fraction wherein the fraction is enriched for DNA fragments that contain an expanded repeat. While it is understood that this method is not limited to the identification of expanded trinucleotide repeats, for purposes of this discussion only expanded trinucleotide repeat will be considered. When RED analysis is performed on a genomic DNA sample that contains multiple trinucleotide expansions, the RED ladder generated from each expansion is superimposed on one another and the size of the largest ligation product corresponds with the approximate size of the largest expansion. In 2D-RED analysis the multiple expansions present in a genomic sample are physically separated from one another prior to RED analysis, preferably using size-fractionation of genomic restriction fragments. In addition to identifying an enriched genomic size fraction for use in subsequent cloning and isolation procedures, the 2D-RED assay measures both the number and size of the expansions present in the genome. Analysis of CAG trinucleotide repeats using 2D-RED analysis has revealed that human genomic DNA samples contain two to four size fractions that typically generate a CAG RED30 product, a single size fraction that typically generates a RED40 product, and a small but variable number of fractions that generate larger RED products (FIG. 7A).

Another aspect of this invention relates to a method for isolating expanded trinucleotide repeats and corresponding flanking sequence from genomic DNA. This method of Repeat Analysis, Pooled Isolation, and Detection of individual RED-positive clones (RAPID cloning) uses the RED assay to follow the expanded repeat through a series of pooled enrichment steps until a single RED-positive clone is obtained. This method can be divided into 1) fractionating a population of DNA fragments and detecting the fraction that contains an extended repeat; 2) cloning the DNA fragments contained in the fraction of DNA that contains an extended repeat; and 3) identifying clones that contain the extended repeat. The fractionation step can be further divided into 1) digesting genomic DNA with a restriction enzyme to obtain DNA fragments; 2) resolving the DNA fragments by gel electrophoresis and dividing into fractions on the basis of size; and 3) detecting the presence of an extended trinucleotide repeat in each size fraction. Preferably, the RED assay is used to detect the presence of an extended trinucleotide repeat in each size fraction.

Using this technology, the expanded SCA7 allele from the genomic DNA of an individual with ataxia and retinal degeneration can be purified and cloned. In addition, a DNA fragment containing a novel expanded repeat can be purified and cloned from the genomic DNA of an individual with clinical features similar to myotonic dystrophy. Isolating the SCA7 and Mn1 CAG repeat expansions and the respective flanking DNA directly from the genomic DNA of single individuals illustrates the advantages of RAPID cloning for the identification of pathogenic repeat expansions for cases in which large pedigrees are unavailable, and demonstrates the dramatically improved efficiency with which putative trinucleotide disease genes can be isolated, characterized, and evaluated.

In many respects a properly optimized method of performing RED analysis provides an ideal assay for tracking novel trinucleotide repeat expansions through purification and cloning procedures and has distinct advantages over other cloning assays that have been described (e.g., stringent hybridization and antibodies to polyglutamine tracts). The use of genomic DNA allows the isolation of any potential trinucleotide repeat expansion regardless of the expression pattern. Utilization of different oligonucleotides in the RED assay allows any of the possible trinucleotide repeats to be detected, and the cycled nature of the reaction makes it extremely sensitive. Most importantly, the ligation component of this assay allows RED to measure the approximate repeat length of the expansion present in the DNA template. The repeat length discrimination provided by RED is maintained as the concentration of target sequence in the template increases. This information provides a clear and robust means of distinctly identifying the expansion target throughout the purification process.

1. Fractionation of DNA Fragments and Detecting the Fraction that Contains an Extended Repeat (2D-RED)

RED analysis involves directly testing a sample of genomic DNA for the presence of an expanded repeat. When RED analysis is performed on a genomic DNA sample that contains multiple trinucleotide expansions, the RED ladder generated from each expansion is superimposed on one another and the size of the largest ligation product corresponds with the approximate size of the largest expansion. Thus, it is difficult to evaluate whether the genomic DNA contains more than one expanded repeat. In 2D-RED analysis the multiple expansions present in a genomic sample are physically separated from one another prior to RED analysis using size-fractionation of genomic restriction fragments. In addition to identifying an enriched genomic size fraction for use in subsequent cloning and isolation procedures, the 2D-RED assay measures both the number and size of the expansions present in the genome. The end result of the fractionating step is the identification of a population of DNA fragments where at least one of the DNA fragments contains an expanded repeat region.

Genomic DNA used in 2D-RED can be isolated from any individual. Preferably, genomic DNA is isolated from a human individual affected with a disease that may be associated with the expansion of a repeat. Any method known to the art for isolating genomic DNA can be used.

Genomic DNA is digested with a restriction enzyme to yield DNA fragments. Any restriction enzyme can be used. Preferably, the restriction enzyme will be Sau3A, MboI or EcoRI. Methods detailing the use of restriction endonucleases to digest DNA can be found in Sambrook et al., *Molecular Cloning: A Laboratory Manual*; Cold Spring Harbor Laboratory: New York (1989).

Digested DNA is resolved to divide the population of DNA fragments by size. The DNA fragments can be resolved by any method available. Preferably, digested DNA will be resolved by gel electrophoresis. More preferably by gel electrophoresis with low melting-point agarose. The resolved DNA is separated into discrete size fractions. For instance, if the DNA fragments were resolved by gel electrophoresis, the portion of the gel containing the DNA fragments can be excised with a razor blade. This gel segment can then be dissected into uniform slices using, for instance, a gel-slicing device. After separation of the DNA fragments into separate fractions, the DNA fragments in each fraction can be purified.

To detect those fractions that contain at least one DNA fragment that contains an expanded repeat, any assay for detecting an expanded repeat can be used. Preferably, each fraction is subjected to RED analysis. The oligonucleotide used in RED analysis is preferably 5' phosphorylated. Any oligonucleotide that is complementary to the repeat that is being analyzed can be used. For instance, to detect the presence of the CAG repeat, an oligonucleotide with multiple repeats of the sequence CTG would be used. Preferably, when the repeat is a trinucleotide repeat the total length of the oligonucleotide will be 30 nucleotides. RED analysis can be performed as described (Schalling, M., et al., *Nature Genetics*, 4, 135–139 (1993), Lindblad, K., et al., *Nature Genetics*, 7, 124 (1994), Lindblad, K., et al., *Genome Research*, 6, 965–971 (1996)). One aspect of this invention involves identifying expanded trinucleotide repeats from genomic DNA comprising performing RED analysis on a sample of genomic DNA wherein the rate of temperature change from the denaturation temperature is decreased from approximately 0.1 second per degree, and wherein the ligation buffer contains formamide. Thus, the rate of temperature change from the denaturation temperature is less than approximately 0.1 second per degree, preferably the rate of temperature change from the denaturation temperature is decreased to 2 seconds per degree, and the ligation buffer contains 4% formamide.

The products of the assay to detect the presence of an expanded repeat in each fraction are resolved. This allows the products of the assay to be detected. For instance, if RED analysis was performed, the RED products are resolved by gel electrophoresis. Detection of the products can be by any method. Preferably, the products are transferred to a membrane and detected by hybridization with a labeled DNA probe that is complementary to the sequence of the oligonucleotide used to detect the expanded repeat. For instance, when RED analysis is performed with the $(CTG)_{10}$ 30-mer, the probe used to detect the product of RED analysis would be a $(CAG)_{10}$ 30-mer.

2. Cloning Sequences Flanking a CAG Repeat

Following identification of a DNA fraction containing at least one extended repeat, the DNA fragments present in the fraction are cloned. Cloning provides for the eventual isolation of a single DNA fragment that contains an extended repeat. Moreover, cloning a single DNA fragment that contains an extended repeat allows the nucleotides flanking the extended repeat to be determined.

The DNA fragments present in the DNA fraction containing at least one extended repeat is preferably inserted into a replicable vector for further cloning (amplification of the DNA). Many vectors are available, and each replicable vector contains various structural components depending on the host cell with which it is compatible. These components are described in detail below.

Construction of suitable vectors employs standard ligation techniques known in the art. Isolated vectors and DNA fragments are cleaved, tailored, and religated in the form desired to generate the recombinant vectors required. Typically, the ligation mixtures are used to transform *E. coli* K12 strain 294 (ATCC 31,446) and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9, 309 (1981) and Maxam et al., *Methods in Enzymology*, 65, 499 (1980).

Alternatively and preferably, the DNA fragments present in the DNA fraction containing at least one extended repeat are inserted into a lamba vector. The resulting recombinant vectors are used to transduce a suitable bacterial strain.

Suitable host cells for cloning or expressing the vectors described here are prokaryotes including eubacteria, such as Gram-negative or Gram-positive organisms, for example, *E. coli, Bacillus* species such as *B. subtilis, Pseudomonas* species such as *P. aeruginosa, Salmonella typhimurium*, or *Serratia marcsecans*. Preferred *E. coli* cloning hosts *E. coli* 294 (ATCC 31,446), *E. coli* XL1_Blue MRF', *E. coli* SOLR, and *E. coli* CJ236, although other strains such as *E. coli* B, *E. coli* χ1776 (ATCC 31,537), and *E. coli* W3110 (ATCC 27,325) are suitable. These examples are illustrative rather than limiting.

Host cells are transformed and preferably transduced with the above-described cloning vectors for this aspect of the invention and cultured in conventional nutrient media modified as appropriate, selecting transductants, and amplifying the genes encoding the desired sequences.

Transduction means introducing DNA into an organism so that the DNA is replicable, either as an extrachromosomal element or by chromosomal integrant. The vector used in transduction is typically derived from a bacteriophage, preferably lambda. Following ligation of insert DNA fragments with the bacteriophage vector, the recombinant bacteriophage vector is packaged into the appropriate protein phage particle. The resulting population of phage particles is used to infect an appropriate bacterial strain. Depending on the host cell and phage used, transduction is done using standard techniques appropriate to such cells.

After cloning the DNA fragments present in the fraction that contains at least one extended repeat, the individual clones that contain the extended repeat are identified and isolated. One method to identify the individual clone involves screening the entire library of clones by plating host cells containing the library of clones on an appropriate media. The media optionally contains an appropriate selective agent, preferably an antibiotic. The individual colonies or plaques are then assayed by methods well known in the art, including hybridization with a labeled DNA probe that is complementary to the sequence of the oligonucleotide used to detect the expanded repeat.

Alternatively and preferably, the library of clones will be used in several post-cloning enrichment steps. These steps are similar to procedures well known in the art (Ostrander et al., *Proc. Natl. Acad. Sci U.S.A.*, 89, 3419–3423 (1992), Kunkel et al., (*Methods in Enzymology*, 154, 367–382 (1987)). The result is the identification of individual clones, each of which contains a DNA fragment containing a trinucleotide repeat.

After isolation of individual clones, the nucleotide sequence of the DNA flanking the CAG repeats can be determined by techniques well known to the art. The sequence of the flanking DNA can be used to locate the position of the DNA on a physical map using techniques well known to the art. The sequence of the flanking DNA can also be used to clone the full length gene.

3. Cloning Full Length Genes Using Sequences that Flank an Extended Repeat

The present invention relates to nucleic acid molecules containing an extended repeat, including nucleic acid molecules corresponding to entire genes containing an extended repeat and portions thereof. Preferably the extended repeat is the CAG repeat region of an isolated spinocerebellar ataxia type 7 gene, and nucleic acid molecules corresponding to the entire SCA7 gene and portions thereof. The present invention further relates to vectors and isolated recombinant vectors comprising the entire SCA7 gene and portions thereof, including an isolated recombinant vector comprising the nucleotides of SEQ ID NO:1 or SEQ ID NO:2 operatively linked to heterologous vector sequences.

As used herein, the term "isolated" means that the nucleic acid molecule, gene, or oligonucleotide is essentially free from the remainder of the human genome and associated cellular or other impurities. This does not mean that the product has to have been extracted from the human genome; rather, the product could be a synthetic or cloned product for example. As used herein, the term "nucleic acid molecule" means any single or double-stranded RNA or DNA molecule, such as mRNA, cDNA, and genomic DNA.

Cloning of DNA into the appropriate replicable vectors provides for determining the sequences that flank an extended repeat and subsequent isolation of the full length gene. Cloning allows expression of the gene product and makes the gene available for further genetic engineering. Expression of the gene product or portions thereof is useful because these gene products can be used as antigens to produce antibodies, as described in more detail below, and in U.S. patent application Ser. No. 08/267,803, filed Jun. 28, 1994.

1. Isolation of DNA

DNA containing a gene containing an expanded repeat may be obtained from any cDNA library prepared from tissue believed to possess the mRNA encoded by the gene and to express it at a detectable level. Optionally, the SCA7 gene may be obtained from a genomic DNA library or by in vitro oligonucleotide synthesis from the complete nucleotide or amino acid sequence.

Libraries are screened with appropriate probes designed to identify the gene of interest or the protein encoded by it. Preferably, the probes are derived from the nucleotide sequence flanking the extended repeat. Screening the cDNA or genomic library with the selected probe may be accomplished using standard procedures. Screening cDNA libraries using synthetic oligonucleotides as probes is a preferred method of practicing this invention. The oligonucleotide sequences selected as probes should be of sufficient length and sufficiently unambiguous to minimize false positives. When screening a library that contains DNA from different species, the actual nucleotide sequence(s) of the probe(s) is usually designed based on regions of the nucleotides flanking the extended repeat that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Embodiments of nucleic acid molecules of this invention include isolated DNA fragments comprising bases 1–128 of SEQ ID NO:1, bases 286–476 of SEQ ID NO:1, bases 1–128 of SEQ ID NO:1 and further comprising a CAG repeat region and bases 1–128 of SEQ ID NO:1 in a vector. Other embodiments of nucleic acid molecules of this invention include isolated DNA fragments comprising bases 922–1002 of SEQ ID NO:2, bases 1033–1864 of SEQ ID NO:2, bases 922–1002 of SEQ ID NO:2 and further comprising a CAG repeat region, and bases 922–1002 of SEQ ID NO:2 in a vector.

Of particular interest is the SCA7 nucleic acid that encodes a full-length mRNA transcript, including the complete coding region for the gene product, ataxin-7. Nucleic acid containing the complete coding region can be obtained by screening selected cDNA libraries using the deduced amino acid sequence.

An alternative means to isolate the gene containing an expanded repeat is to use PCR methodology. This method requires the use of oligonucleotide primer probes that will hybridize to the SCA7 gene. Strategies for selection of PCR primer oligonucleotides are described below.

2. Insertion of DNA into Vector

The nucleic acid (e.g., cDNA or genomic DNA) containing the gene containing an expanded repeat is preferably inserted into a replicable vector for further cloning (amplification of the DNA) or for expression of the gene product. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector.

Construction of suitable vectors employs standard ligation techniques known in the art. Isolated plasmids or DNA fragments are cleaved, tailored, and religated in the form desired to generate the plasmids required. Typically, the ligation mixtures are used to transform E. coli K12 strain 294 (ATCC 31,446) and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9,309 (1981) and Maxam et al., *Methods in Enzymology*, 65, 499 (1980).

Replicable cloning and expression vector components generally include, but are not limited to, one or more of the following: a signal sequence, an origin of replication, one or more marker genes, an enhancer element, a promoter and a transcription termination sequence. At this time a large number of each of these components that are recognized by a variety of potential host cells are well known to the art. It is also well known to the art that a component can be removed from its source DNA using standard molecular biology techniques and used in conjunction with other components that are endogenous to a particular species, e.g., prokaryotes, filamentous fungi, yeast, protozoa, and vertebrate, invertebrate and plant cell culture. Alternatively, heterologous components can be used together to result in the stable replication of a cloned DNA, or the expression of a protein encoded by a cloned DNA. A non-limiting description of components that can be used in cloning genes containing expanded trinucleotide repeats can be found in U.S. patent application Ser. No. 08/267,803, filed Jun. 28, 1994.

3. Host Cells

Suitable host cells for cloning or expressing the vectors herein are prokaryotes, filamentous fungi, yeast, protozoa, and higher eukaryotic cells including vertebrate, invertebrate and plant cells. Preferably the host cell should secrete minimal amounts of proteolytic enzymes.

Suitable host cells for the expression of a glycosylated protein encoded by a gene containing an expanded repeat are derived from multicellular organisms. Such host cells are capable of complex processing and glycosylation activities. In principle, any higher eukaryotic cell culture is workable, whether from vertebrate or invertebrate culture.

Propagation of vectors containing cloned DNA in host cells has become a routine procedure in recent years and is well known to the art.

Alternatively, in vitro methods of cloning, e.g., PCR or other nucleic acid polymerase reactions, are suitable.

4. Transfection and Transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Numerous methods of treating a host cell to promote the uptake of a vector containing cloned DNA are known to the art including, for example, calcium phosphate precipitation, electroporation, calcium chloride treatment, nuclear injection, protoplast fusion or microprojectile bombardment may also be used.

The culture of host cells containing the cloning vector in suitable media so as to promote viability of the host cells and carriage of the cloning vector is well known to the art. Any necessary supplements may also be included at appropriate concentrations that would be known to those skilled in the art. The culture conditions, such as temperature, pH, and the like will be apparent to the ordinarily skilled artisan. The host cells referred to in this disclosure encompass in vitro culture as well as cells that are within a host animal.

C. Protein

A gene containing an extended repeat encodes a protein that can be purified from a host cell expressing the recombinant gene. For instance, the SCA7 gene encodes a novel protein, ataxin-7, a representative example of which is shown in SEQ ID NO:12, and a portion of which is shown in SEQ ID NO:11. Thus, the present invention is related to polypeptides comprising amino acids encoded by the nucleic acids of genes containing an extended trinucleotide repeat, preferably the nucleic acid of SEQ ID NO:1 or SEQ ID NO:2. The present invention is also related to an isolated recombinant vector and an isolated nucleic acid fragment that is capable of expressing a polypeptide comprising amino acids of a protein that contains a polyglutamine region. Preferably, the amino acids comprise amino acids 1–27 of SEQ ID NO:11 or SEQ ID NO:12. The invention is further related to a protein encoded by the SCA7 gene, wherein the protein contains between 5 and 110 CAG repeats and has a molecular weight of approxiamtely 95–108 kD.

It is to be understood that ataxin-7 represents a set of proteins produced from the SCA7 gene with its unstable CAG region. Ataxin-7 can be produced from cell cultures. With the aid of recombinant DNA techniques, synthetic DNA and cDNA coding for ataxin-7 can be introduced into microorganisms which can then be made to produce the peptide. It is also possible to manufacture ataxin-7 synthetically, in a manner such as is known for peptide syntheses.

Ataxin-7 is preferably recovered from the culture medium as a cytosolic polypeptide, although it can also be recovered as a secreted polypeptide when expressed with a secretory signal.

Ataxin-7 can be purified from recombinant cell proteins or polypeptides to obtain preparations that are substantially homogenous as ataxin-7 using techniques well known to the art. The following procedures are exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; ligand affinity chromatography, using, e.g., protein A Sepharose columns to remove contaminants such as IgG.

Ataxin-7 variants in which residues have been deleted, inserted, or substituted are recovered in the same fashion as native ataxin-7, taking account of any substantial changes in properties occasioned by the variation. A protease inhibitor such as phenyl methyl sulfonyl fluoride (PMSF) also may be useful to inhibit proteolytic degradation during purification, and antibiotics may be included to prevent the growth of adventitious contaminants.

Covalent modifications of both native ataxin-7 and amino acid sequence variants of the ataxin-7 may be covalently modified. Covalent modifications of ataxin-7 or fragments thereof can be introduced into the molecule by reacting targeted amino acid residues of the ataxin-7 or fragments thereof with a derivatizing agent capable of reacting with selected side chains or the N- or C-terminal residues.

D. Antibodies

The present invention also relates to polyclonal or monoclonal antibodies raised against a full length protein encoded by a gene containing an extended repeat, or a fragment thereof (preferably fragments having 8–40 amino acids, more preferably 10–20 amino acids, that form the surface of the folded protein), or variants thereof, and to diagnostic methods based on the use of such antibodies, including but not limited to Western blotting and ELISA (enzyme-linked immunosorbant assay). For instance, the present invention relates to polyclonal or monoclonal antibodies raised against ataxin-7 or ataxin-7 fragments, and to diagnostic methods based on the use of such antibodies.

Polyclonal antibodies to the SCA7 polypeptide generally are raised in animals by multiple subcutaneous (sc) or intraperitoneal (ip) injections of ataxin-7, ataxin-7 fragments, or variants thereof, and an adjuvant using techniques well known to the art. The route and schedule of immunizing a host animal or removing and culturing antibody-producing cells are variable and are generally in keeping with established and conventional techniques for antibody stimulation and production. Serum antibodies (IgG) are purified via protein purification protocols that are well known in the art.

Monoclonal antibodies are prepared by recovering immune cells—typically spleen cells or lymphocytes from lymph node tissue—from immunized animals (usually mice) and immortalizing the cells in conventional fashion, e.g., by fusion with myeloma cells. The hybridoma technique described originally by Kohler et al., *Eur. J. Immunol.*, 6, 511 (1976) has been widely applied to produce hybrid cell lines that secrete high levels of monoclonal antibodies against many specific antigens. The production and purification of monoclonal antibodies is well known to the art.

The anti-ataxin-7 antibody preparations of the present invention are specific to ataxin-7 and do not react immunochemically with other substances in a manner that would interfere with a given use. For example, they can be used to screen for the presence of ataxin-7 in tissue extracts to determine tissue-specific expression levels of ataxin-7.

The present invention also encompasses an immunochemical assay that involves subjecting antibodies directed against ataxin-7 to reaction with the ataxin-7 present in a sample to thus form an (ataxin-7/anti-ataxin-7) immune complex, the formation and amount of which are measures—qualitative and quantitative, respectively—of the ataxin-7 presence in the sample. The addition of other reagents capable of biospecifically reacting with constituents of the protein/antibody complex, such as anti-antibodies provided with analytically detectable groups, facilitates detection and quantification of ataxin-7 in biological samples, and is especially useful for quantitating the level of ataxin-7 in biological samples. ataxin-7/anti-ataxin-7 complexes can also be subjected to amino acid sequencing using methods well known in the art to determine the length of a polyglutamine region and thereby provide information about likelihood of affliction with spinocerebellar ataxia and likely age of onset. Competitive inhibition and non-competitive methods, precipitation methods, heterogeneous and homogeneous methods, various methods named according to the analytically detectable group employed, immunoelectrophoresis, particle agglutination, immunodiffusion and immunohistochemical methods employing labeled antibodies may all be used in connection with the immune assay described above.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL SECTION

RAPID cloning was used to identify, characterize and evaluate two novel CAG expansions. The first CAG expansion was isolated from the genomic DNA of an individual with a genetically distinct form of myotonic dystrophy. The second CAG expansion was isolated from the genomic DNA of an individual with ataxia and retinopathy. These results demonstrate the advantages of RAPID cloning for the identification of pathogenic repeat expansions for cases in which large pedigrees are unavailable, and illustrates the dramatically improved efficiency with which putative trinucleotide disease genes can be isolated, characterized and evaluated.

A. Methods

1. Clinical Resources.

The ataxia patients were collected and examined as described (Ranum, L. P. W. et al., *Am. J. Hum. Genet.*, 57, 603–608 (1995)). For the family with a genetically distinct form of myotonic dystrophy, neurological exams and EMG's were performed with the presence of myotonic discharges used as the diagnostic criteria for the classification of MN1 family members as affected. After informed consent was obtained, blood was collected in two acid citrate dextrose (ACD) tubes (Vacutainer #4606) and one sodium heparin tube (Vacutainer #6480). DNA was isolated from blood in the ACD tubes (Puregene #D-5003, Gentra Systems, Research Triangle Park, N.C.) and EBV transformed lymphoblastiod cell lines (LCLs) were established using blood from the heparin tubes.

DNA samples from the grandparents of the panel of 40 Centre d'Etude du Ploymorphisme Humain (CEPH) reference families were used as normal controls for the SCA7 PCR assay (Marx, J. *Science*, 229, 150–151 (1985)).

2. Optimized RED Conditions.

RED analysis was performed as described by Schalling et al.; and Lindblad et al., (Schalling, M., et al., *Nature Genetics,* 4, 135–139 (1993), Lindblad, K., et al., *Nature Genetics,* 7, 124 (1994), and Lindblad, K. et al., *Genome Research,* 6, 965–971 (1996) with the following modifications: 2 mg of genomic DNA were used; 4% formamide was added to the reaction, the reaction conditions were denaturation at 94° C. (4 min, 50 sec) followed by 495 cycles of 94° C. for 10 seconds, and 70° C. to 78° C. for 40 seconds; a 2 sec/degree ramp was used when the reaction temperature dropped from 94° C. The oligonucleotide used in the RED reaction is a PAGE purified, 5' phosphorylated, $(CTG)_{10}$ 30-mer synthesized by National Biosciences Inc., (Plymouth, Minn.). All reactions were performed using an Omnigene Hybaid thermal cycler with a heated lid. RED products were separated by size on a denaturing 6% polyacrylamide gel containing 6M urea and transferred to Hybond N+ (Amersham) as described (Schalling, M., et al., *Nature Genetics* 4, 135–139 (1993), Lindblad, K., et al., *Nature Genetics,* 7, 124 (1994), Lindblad, K. et al., *Genome Research,* 6, 965–971 (1996)), and hybridized with a 3' labeled $(CAG)_{10}$ 30 mer.

3. Two Dimensional RED (2D-RED) Analysis of Genomic DNA.

Ten mg of genomic DNA was digested with a restriction enzyme and size-separated on a 1.5% SeaPlaque GTG (FMC, Rockland, Me.) low melting-point agarose gel in 1× TAE buffer. The DNA was visualized after ethidium bromide staining on a UV transilluminator and the portion of the gel containing DNA was excised with a razor blade. This gel segment was then dissected into uniform 2 mm slices using a gel-slicing device in which microscope coverslips are used as disposable dissecting blades. These slices were placed in separate 0.5 ml PCR tubes, heated to 72° C. for 10 min to melt, and then equilibrated at 42° C. One µl AgarACE enzyme (0.2 U, Promega, Madison, Wis.) was added and the samples were incubated for 3 hour to completely digest the agarose. The size separated DNA was concentrated by EtOH precipitation, dried, and resuspended in 7 µl of 10 mM Tris, 1 mM EDTA (pH 7.5) buffer. RED analysis was performed on 3.5 µl of DNA from each fraction to determine which size fraction was most highly enriched for the RED positive genomic fragments.

4. Cloning of Genomic Fragments.

EcoRI digested genomic DNA recovered from the RED positive gel fraction was cloned using the predigested Lambda ZapII/EcoRI/CIAP cloning and packaging kit (Stratagene, La Jolla, Calif.). After the initial library was generated and titered, eight plates containing $5 \times 10^4$ primary clones/plate were amplified separately as described in the protocols provided by the manufacturer. ssDNA derivatives of these libraries were then generated by coinfecting *E. coli* strain XL1-Blue MRF' with both the amplified lambda library and the ExAssist M13 helper phage. The SK-Bluescript phagemids were used to infect the SOLR strain of *E. coli* (Stratagene, La Jolla, Calif.) from which double stranded plasmid (pBluescript) DNA was purified using the Wizard M13 DNA Purification System (Promega). The plasmid DNA representing each clone pool was then assayed by RED analysis for the presence of expanded repeats.

5. Post-Cloning Enrichment.

The enrichment of CAG containing clones is an adaptation of the general approach described by Ostrander et al., (*Proc. Natl. Acad. Sci U.S.A.,* 89, 3419–3423 (1992)) which is based on the selection schemes established by Kunkel et al., (*Methods in Enzymology,* 154, 367–382 (1987)). Plasmid DNA (~0.1 mg) representing a RED positive pool of clones was electroporated into *E. coli* strain CJ236 (dut-, ung-, BioRad, Hercules, Calif.) to generate uracil-substituted DNA. After a 1 hour recovery without antibiotic, the cells were inoculated into 200 ml of LB containing 40 mg/ml ampicillin and incubated at 37° C. with shaking for 3 hr. To convert the plasmid dsDNA to ssDNA, M13K07 helper phage ($1 \times 10^{10}$ pfu) was added, and the culture was incubated at 37° C. w/ shaking for an additional 2 hrs. Kanamycin was then added to 1%, the culture was incubated for 18 hours and single stranded DNA was purified essentially as described (Vieira, J., et al., *Methods in Enzymology,* 153, 3–11 (1987)), but with the addition of a DNaseI treatment (2000 u, 1 hr, 37° C.) prior to phage precipitation. The purified ssDNA was incubated with T4 DNA polymerase (New England Biolabs, Beverl, Mass.) overnight without dNTP to eliminate contaminating DNA that could act as primers. The CTG repeat containing ssDNA was then converted to dsDNA by primer extension using ampliTaq (Perkin Elmer) and a $(CAG)_{10}$ primer at 72° C. in a buffer containing 4% formamide. One µl of uracil DNA glycosylase (UDG, GIBCO-BRL, Gaithersburg, Md.) was added after extension to degrade the remaining ssDNA. After extraction (1×phenol:CHCl$_3$ and 1×CHCl$_3$) and EtOH precipitation, the DNA was electroporated into the SURE strain of *E. coli* (Stratagene, La Jolla, Calif.).

6. Sequence Analysis.

Genomic sequences from the ends of the SCA7 EcoRI fragment were used in a nucleotide BLAST search of the GenBank database and revealed an overlap with three related EST sequences (accession numbers H40285, H40290, H41756). A search of the human EST map (available on the World Wide Web) (Schuler, G. et al., *Science,* 274, 540–546 (1996)) revealed that these ESTs have been mapped to the same region of chromosome 3p to which the SCA7 mutation has been mapped (Gouw, L.G. et al., *Nature Genetics,* 10, 89–93 (1995), Benomar, A. et al., *Nature Genetics,* 10, 84–88 (1995), and David, G. et at. *American Journal of Human Genetics,* 59, 1328–1336 (1996)). A BLAST search with the nucleotide sequence flanking the SCA7 CAG repeat revealed that an unexpanded allele with ten CAG repeats was present in the database and reported as a chromosome 3 NotI jumping clone (accession number X95831). The sequence flanking the accession number for the MN1 CAG did not match any present in the database.

7. PCR Assays of Expanded Trinucleotide Repeats.

The SCA7 repeat expansion assay was done using the SCA7 -F1 (5' TTTTTTGTTACATTGTAGGAGCG) (SEQ ID NO:5) and SCA7 -R1 (5' CACTTCAGGACTGGGCA-GAG) (SEQ ID NO:6) primers in a PCR reaction (50 ng genomic DNA, 200 mM dNTP, 10 mM Tris pH 9.0, 50 mM KCl, 0.1% Triton X-100, 1.5 mM MgCl$_2$, 10% DMSO, 0.1 units AmpliTaq) cycled 35× (94° C. 50 s, 55° C. 1 min 15 s, 72° C. 1 min).

The MN1 CAG repeat assay was performed using primers MN4F (5' GCCAGATGAGTTTGGTGTAAGAT) (SEQ ID NO:7) and MN4R (5' AAGCCATTTCTCCAAAAGAAG-GTC) (SEQ ID NO:8) were used in a PCR reaction (20 ng genomic DNA, 200 mM dNTP, 10 mM Tris pH 9.0, 50 mM KCl, 0.1% Triton X-100, 0.01% gelatin, 1.5 mM MgCl$_2$, 10% DMSO, 0.1 unit AmpliTaq) cycled 35× (94° C. 45 s, 52° C. 1 min, 72° C. 1 min).

B. Results

1. Optimization of the RED Assay

To determine whether $(CTG)_{10}$ RED analysis worked well, the available protocols (Schalling, M., et al., *Nature*

Figure 2B:
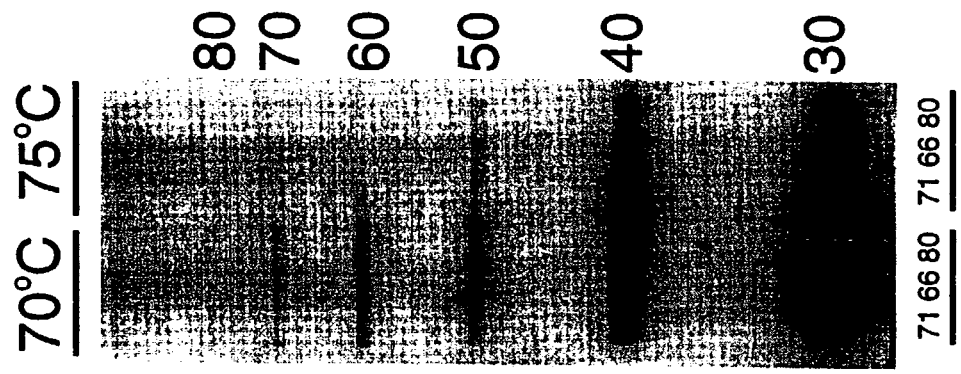
FIG. 2 RED analysis of genomic DNA control samples. A: An optimized RED procedure was performed on genomic DNA from individuals with CAG expansions of known size. The size of the SCA1 (47 CAG repeats), SCA3 (71 repeats), HD (66 repeats) and DM (80 repeats) alleles as measured by PCR assays is shown below the phosphoimage panels. The size of the RED products are indicated at the side of the panel, and the anneal temperature used for the ligation reaction is indicated above. For each genomic sample assayed, the largest RED product corresponds appropriately with the size of the known expanded CAG allele. B: The RED assay was repeated for the SCA3, HD, and DM genomic samples in a reaction buffer that did not contain formamide but was otherwise identical to that used for panel "A".
Figure 2A:
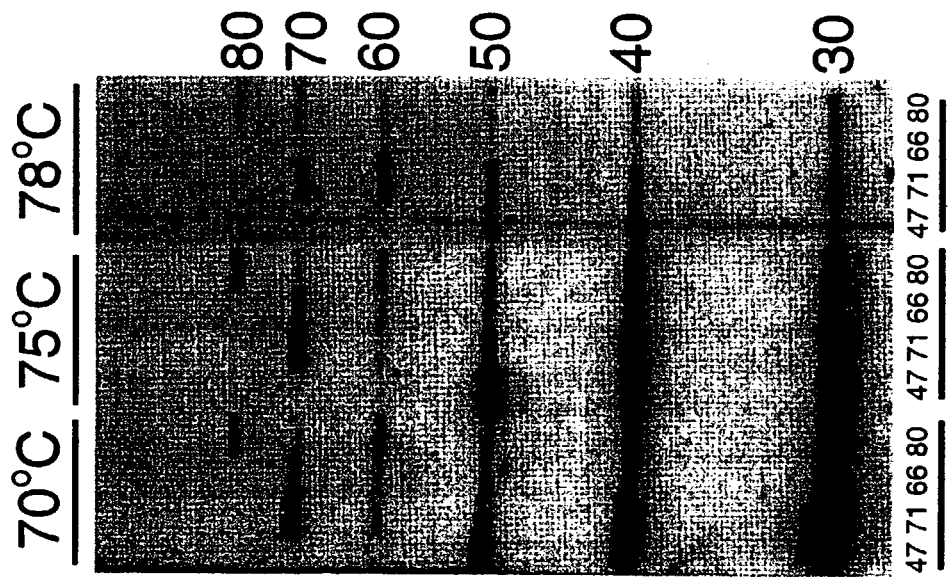

Genetics 4, 135–139 (1993), Lindblad, K., et al., *Nature Genetics* 7, 124 (1994), Lindblad, K. et al., *Genome Research* 6, 965–971 (1996)). were tested with defined genomic DNA control templates. RED results with these templates were inconsistent and typically did not correlate with size of the largest known CAG expansion in the genomic sample. It was found that decreasing the rate of temperature change during annealing and including 4% formamide in the ligation buffer increased the sensitivity and reproducibility of this assay for detecting uninterrupted CAG expansion genomic controls. RED analysis of genomic DNA from individuals with CAG expansions of known size at the SCA7, SCA3, HD, and DM disease loci using this optimized protocol is shown in FIG. 2a. For each of the positive genomic control samples shown, the size of the largest RED product corresponds well with the size of the known CAG expansion as measured by PCR assays. RED analysis of the SCA3, HD, and DM genomic samples using a ligation buffer that did not contain formamide is shown in FIG. 2b. The results obtained from this type of reaction differ dramatically from those shown for the same samples in FIG. 2a. We have found that multiple other alterations to the optimized reaction conditions, including the use of different thermocyclers and poor DNA quality, can have similar deleterious affects on the RED results we obtain.

2. Two-Dimensional RED Analysis

In a second part of this method, a two dimensional repeat expansion detection assay (2D-RED) was developed that uses the physical size of RED positive genomic DNA digestion fragments to uniquely identify multiple expanded alleles in a genomic DNA sample (see FIG. 3). In the 2D-RED protocol, which is outlined schematically in FIG. 3a, genomic DNA was digested with a restriction enzyme, run on an agarose gel, and separated into discrete size fractions. The agarose from each fraction was enzymatically removed, the DNA was concentrated by precipitation, and RED analysis was performed on the fractions. Agarose gel analysis of a portion of the size fractions generated from MboI-digested genomic DNA from an individual with SCA3/MJD is shown in FIG. 3b. The corresponding RED analysis of these fractions is shown in FIG. 3c. In this example, size fractions consisting of DNA fragments of approximately 500 bp in length generate the RED70 product expected for the expanded SCA3 allele present in the original genomic sample.

3. Cloning and Assessment of a Novel Expanded CAG Repeat

Figure 4:
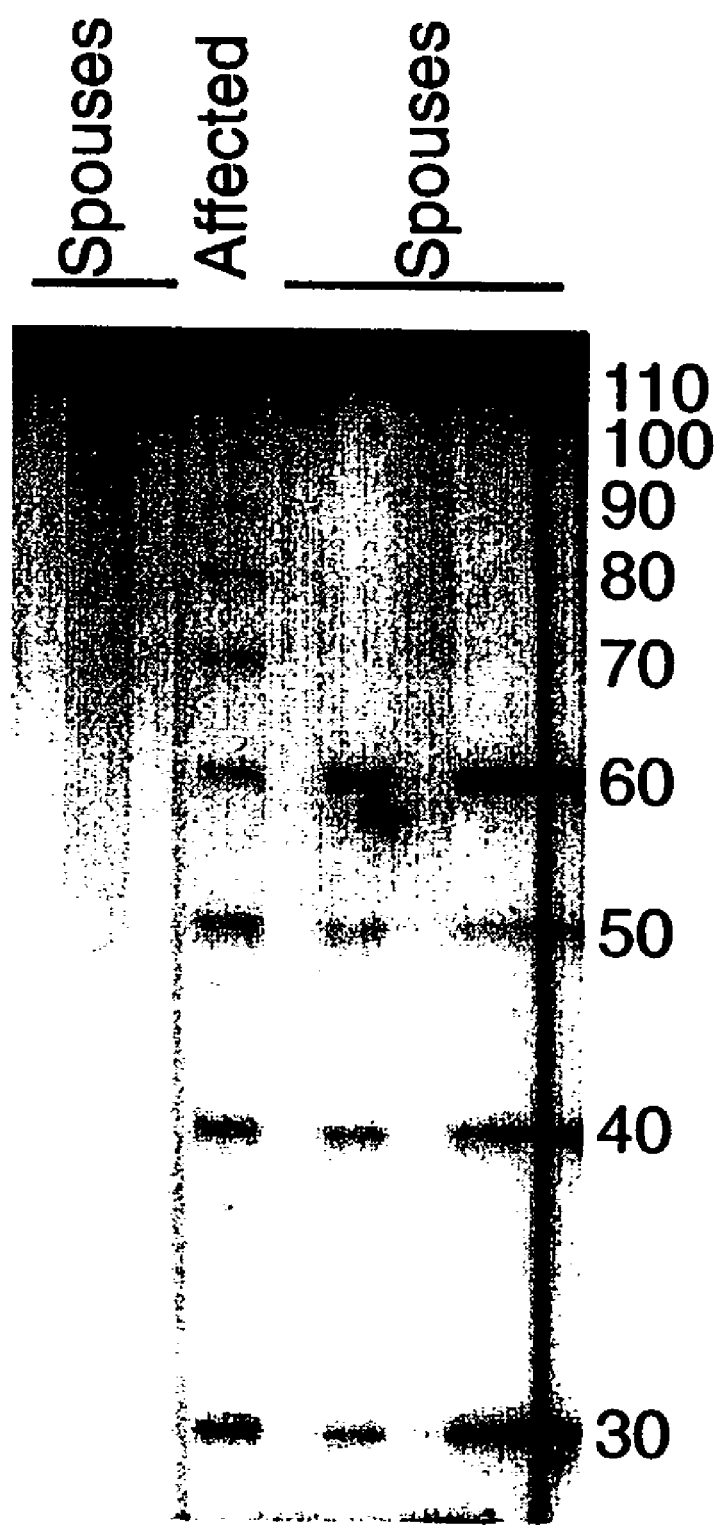
FIG. 4 RED analysis of genomic DNA samples from the MN1 kindred. The RED products generated from one of the affected individuals and from eight spouse samples are shown.

A family (MN1) has been identified that has clinical features strikingly similar to myotonic dystrophy but whose disease locus does not involve the chromosome 19 CTG repeat expansion and is not genetically linked to the DM region of chromosome 19. FIG. 4 shows the results of RED analysis performed on genomic DNA from a control group of eight spouses and one affected member of the MN1 family. The genomic DNA sample from the affected individual generated a RED product that was substantially larger ($\geq 110$ CAG repeats) than any of the products generated by the spouses DNA samples. RED analysis of genomic DNA from additional family members indicated that a CTG-expansion of a similar size was present in at least five other affected individuals and was not detectable in any samples from unaffected family members. 2D-RED analysis of two of the RED positive samples showed that the expansion was present on a MboI fragment of approximately the same size in both genomes. These data suggested the intriguing possibility that a CTG repeat expansion at a locus distinct from DM causes the MN1 form of myotonic dystrophy. To directly assess whether or not the CTG expansion is involved in the disease, we cloned the genomic fragment containing this expansion using the RAPID procedure, sequenced the DNA flanking the repeat and performed PCR analysis of the repeat on the extended kindred.

Figure 5A:
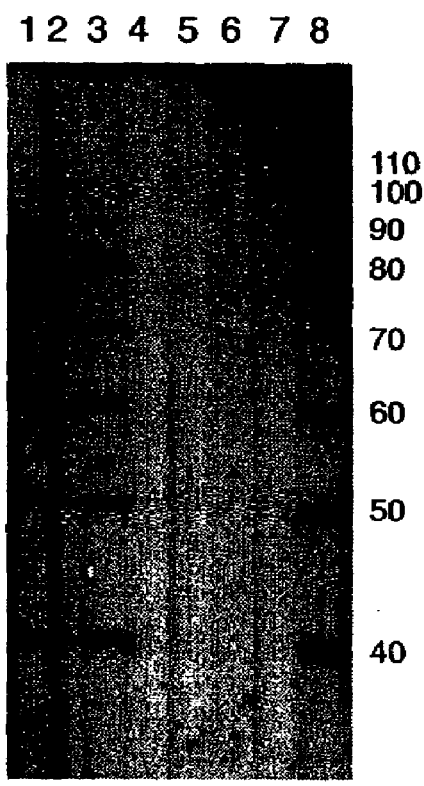
FIG. 5 Cloning and post-cloning enrichment of an expanded CAG repeat from the MN1 kindred. A: RED analysis of plasmid DNA isolated from unenriched clone pools. The 2D-RED size-fractionated genomic DNA containing the long MN1 CAG repeat was cloned into a lambda vector. The resulting library was amplified in pools consisting of approximately $5 \times 10^4$ primary clones and then converted en masse into plasmid library pools. B: Schematic overview of the post-cloning enrichment procedure. A dsDNA library is convened to an ssDNA library in which uracil has been incorporated into the DNA strand. A $(CAG)_{10}$ oligo (SEQ ID NO: 4) is used to prime second-strand synthesis in those clones that contain a long CAG repeaL Uracil-DNA glycosylase (UDG) is then added to remove the uracil residues from the original DNA strand. Transformation of this mixture into E. coli results in the repair and replication of CAG-containing dsDNA clones and in the degradation and elimination of the ssDNA background. C: RED analysis of CAG-enriched clone pools derived from primary pools 3 and 8 (panel B). Each pool contains DNA from 20 individual clones. D: Nucleotide sequence (SEQ ID NO:3) of the genomic DNA flanking the MN1 CAG repeat. The CAG repeat (underlined) varies from 11 to 24 repeats in individuals from the MN1 kindred that do not have an expansion, and has over 100 repeats in individuals with an expansion.
Figure 5C:
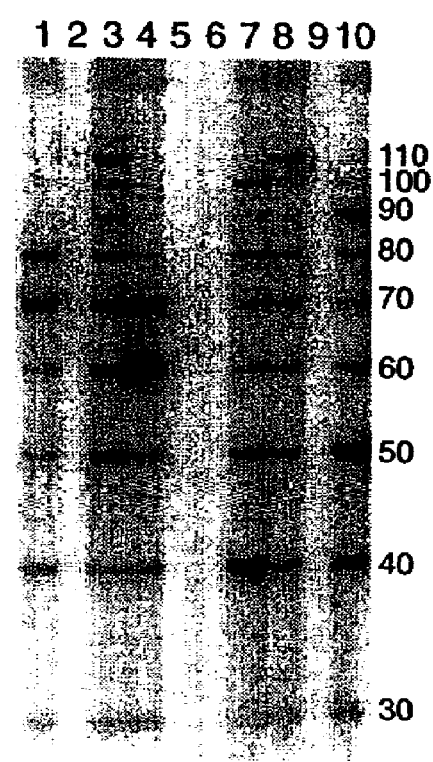
Figure 5B:
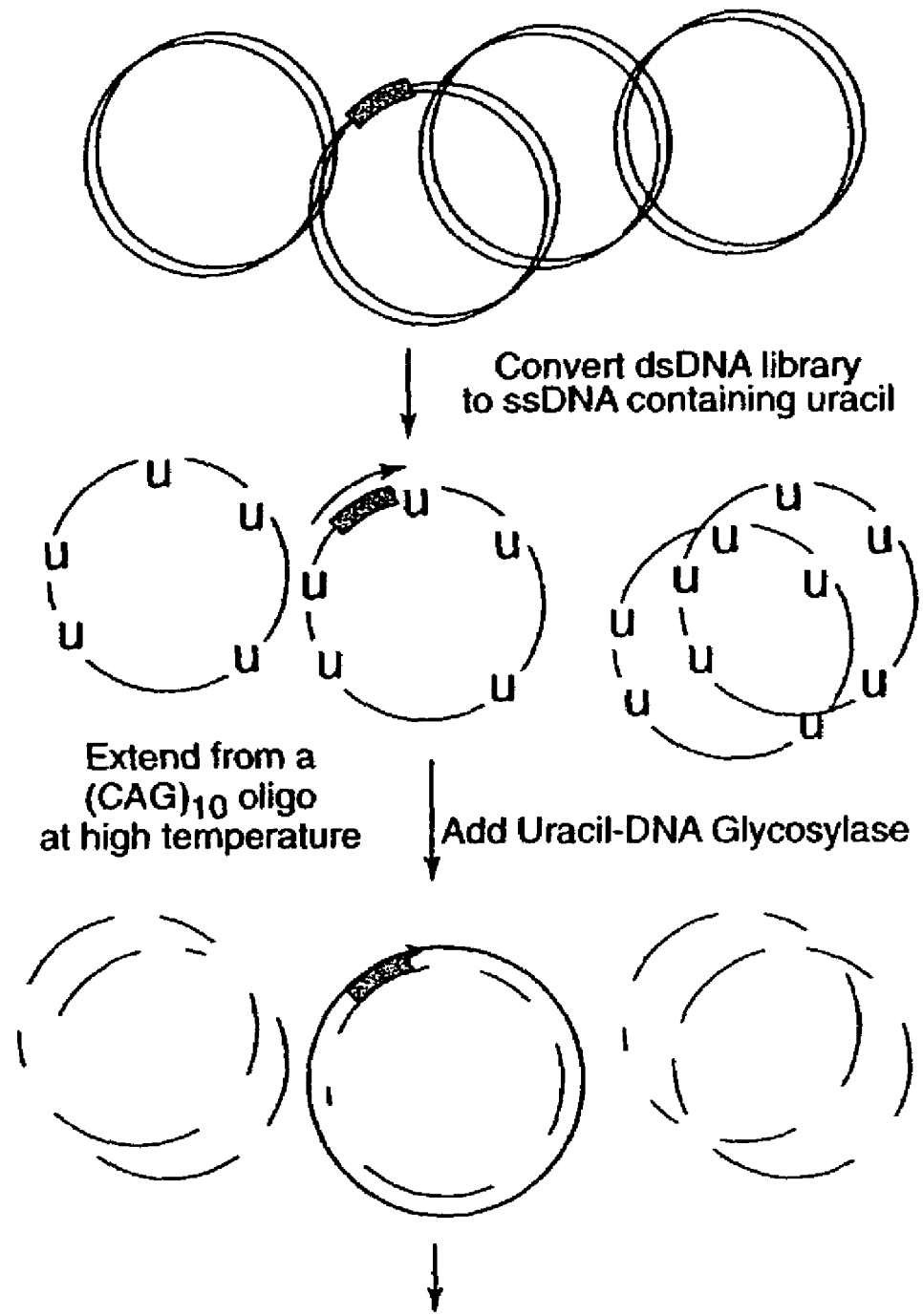

Genomic DNA from an affected member of the MN1 kindred was digested with EcoRI and 2D-RED was performed to identify the RED-positive size fraction. The DNA fragments from this fraction (approximately 2-kb in size) were then cloned into lamdba ZAPII cloning vector (Stratagene). Eight pools consisting of approximately $5 \times 10^4$ primary clones each were amplified and mass excision was performed on each pool separately to convert the lambda clones into plasmids (see Methods). RED analysis was performed on the isolated plasmid DNA from these eight pools to determine which contained the cloned repeat (FIG. 5A). Four of the eight pools were RED positive, and the DNA from two of these (pools 3 and 8) were selectively enriched for CAG-containing clones (FIG. 5B, see Methods). The DNA from small pools of individually inoculated clones (20 clones each) from this enriched library were assayed by RED (FIG. 5C). Individual repeat-containing clones were identified by RED analysis of DNA prepared from row and column pools inoculated from RED positive plates. The genomic inserts from four of these clones were sequenced. All four contained genomic inserts with an identical nucleotide sequences that varied only in the size of the CAG repeat.

The genomic sequence flanking the CAG expansion isolated from the MN1 family is shown in FIG. 5D. The size of the CAG repeat (underlined) varied in the clones obtained up to a maximum length of 110 uninterrupted repeats, a length that corresponds well with the RED results obtained from the genomic DNA of the individual from whom it was isolated. Once an isolated clone was obtained, however, the insert appeared to be stable. In each case, the size of the repeat as determined by sequencing corresponded with the approximate size indicated by RED (see FIG. 5C).

Figure 6:
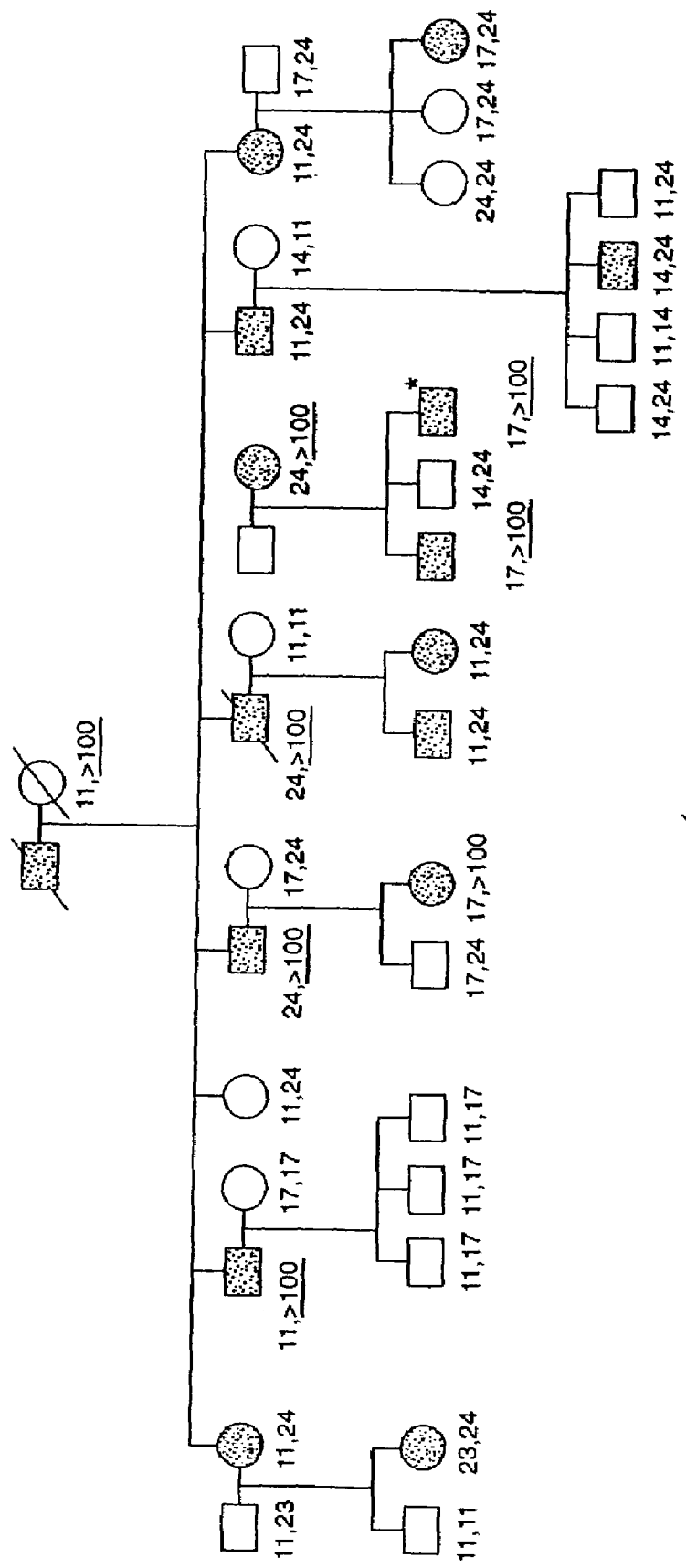
FIG. 6 Pedigree of the MN1 kindred. The number of CAG repeats in each allele of the MN1 CAG repeat sequence is indicated numerically, and the individual from whom the expanded CAG was isolated is starred.

PCR primers were designed from this sequence to amplify across the CAG repeat and PCR analysis of the MN1 kindred was performed (see Methods). This analysis, the results of which are summarized in FIG. 6, showed that the unstable expansion does not cosegregate with the disease. The unexpanded allele was highly polymorphic and had between 11 and 24 uninterrupted CAG repeats (as confirmed by sequence analysis of several alleles). The expanded allele varied in size between individuals and had up to approximately 130 repeats in the individual with the largest expansion. Each of the family members with an expansion at this allele were detected in the original genomic RED analysis, with the exception of the two deceased individuals for whom only relatively poor-quality DNA samples were available.

4. Cloning of the Expanded SCA7 CAG Repeat.

This invention also relates to the isolation of nucleic acid containing a CAG repeat region, hereinafter referred to as SCA7. During the past four years we have collected blood samples from affected individuals representing 355 different families with dominant, recessive or sporadic forms of adult onset ataxia (Ranum, L. P. W. et al., *Am. J. Hum. Genet.*1 57, 603–608 (1995)). To identify individuals whose ataxia was likely to be caused by a novel trinucleotide repeat expansion, we selected patients that were negative for the known dominant ataxia gene expansions (SCA7, 2, 3, and 6), and who had a dominant family history with anticipation. The proband of pedigree A (FIG. 8) fit the above criteria. In addition to having a severe form of olivopontocerebellar degeneration that required nursing home care at 32 yrs of age, the patient also had the retinal degeneration characteristic of patients with SCA7.

Genomic DNA from the proband of kindred A (FIG. 8) was digested with EcoRI and 2D-RED was performed to identify the RED-positive size fractions (FIG. 7A). The DNA fragments from the fraction that generated a RED60 product were then cloned into a lambda vector. Ten pools consisting of approximately $5 \times 10^4$ primary lambda clones each were amplified in pools and mass excision was performed on each pool separately to convert the lambda clones into plasmids and RED analysis was performed on the isolated plasmid DNA from these pools. The DNA from a RED positive clone pool was selectively enriched for CAG-containing clones and DNA from small pools of clones (36 clones in each pool) from this enriched library were assayed by RED (FIG. 7B). RED analysis of DNA prepared from clones individually inoculated from a RED positive plate identified two clones that contained the expanded CAG repeat and the genomic inserts from these clones were sequenced. Sequence analysis (see Methods) revealed that one end of the genomic EcoRI fragment overlaps with a set of ESTs that have been mapped to the SCA7 region of chromosome 3p, which in turn physically mapped the CAG expansion on this genomic fragment to the same region.

The genomic sequence flanking the CAG expansion isolated from the patient with ataxia and retinal degeneration is shown in FIG. 7C. PCR primers were designed from this sequence to amplify across the CAG repeat and PCR analysis was performed on samples from five kindreds in our ataxia family collection that have been diagnosed with retinopathy as well as on a large panel of unaffected control genomic DNA control templates. This analysis, the results of which are summarized in FIG. 8, showed that the CAG repeat sequence is expanded in affected and one at-risk individual (37 to 68 repeats) in these ataxia kindreds but not in any of the unaffected controls. As is the case with other ataxia CAG mutations, the expanded allele is unstable and the age of onset and the repeat size are inversely correlated. Marked anticipation is observed for both male and female transmissions.

Patents, patent applications and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. A method of determining the presence or absence of a polymorphic CAG trinucleotide repeat in a human patient comprising determining the presence of a polymorphic CAG trinucleotide repeat in a CAG repeat region of a spinocerebellar ataxia, type 7 gene in a nucleic acid sample from said patient, and determining the size of the polymorphic CAG trinucleotide repeat wherein the presence of a polymorphic CAG trinucleotide repeat is determined by amplification of nucleic acid containing the CAG trinucleotide repeat using a pair of oligonucleotide primers which specifically amplify the region of nucleic acid containing the expanded CAG trinucleotide repeat, and detecting amplified products containing the CAG trinucleotide repeat region, wherein the oligonucleotide primers comprise SEQ ID NO:5 and SEQ ID NO:6.

2. A method for determining whether a human is at risk for development of spinocerebellar ataxia type 7, the method comprising conducting an assay on a nucleic acid sample from said human to determine the presence or absence of an expanded CAG trinucleotide repeat in a CAG repeat region of a spinocerebellar ataxia type 7 gene, wherein the presence of an expanded CAG trinucleotide repeat having the sequence $(CAG)_n$, wherein $n \geq 30$, is indicative tat said human is at risk for development of spinocerebellar ataxia type 7, wherein said assay comprises:

a) amplifying a target portion of the nucleic acid using a pair of oligonucleotide primers which specifically amplify the region of nucleic acid containing CAG trinucleotide repeats to obtain an amplified product, wherein the oligonucleotide primers are SEQ ID NO:5 and SEQ ID NO:6;
   b) determining the presence or absence of an expanded CAG trinucleotide repeat in said nucleotide sequence of said amplified product; and
   c) determining that said human is at risk for development of SCA7 when $n \geq 30$.

3. The method of claim 2 wherein $n \geq 37$.

4. The method of claim 2 wherein $n \geq 38$.

5. A method for diagnosing spinocerebellar ataxia type 7 in a human patient, said method comprising detennining the presence or absence of an expanded CAG trinucleotide repeat in a CAG repeat region in a spinocerebellar ataxia type 7 gene in a nucleic acid sample from said patient, wherein the presence of an expanded CAG trinucleotide repeat having the sequence $(CAG)_n$, wherein $n \geq 30$, is indicative of spinocerebellar ataxia type 7 in said patient, wherein the presence of an expanded CAG trinucleotide repeat is determined by amplification of nucleic acid containing the CAG trinucleotide repeat using a pair of oligonucleotide primers which specifically amplify the region of nucleic acid containing the expanded CAG trinucleotide repeat, detecting amplified products containing the CAG trinucleotide repeat reaion, wherein the oligonucleotide primers are SEQ ID NO:5 and SEQ ID NO:6, and determining that said human has SCA7 when $n \geq 30$.

6. The method of claim 5 wherein $n \geq 37$.

7. The method of claim 5 wherein $n \geq 38$.

8. A method for diagnosing spinocerebeliar ataxia type 7 in a human, said method comprising:
   a) contacting nucleic acid from said human with oligonucleotide primers that amplify a region of nucleic acid containing CAG trinucleotide repeats in a CAG repeat region of a spinocerebellar ataxia type 7 gene, wherein the oligonucleotide primers are SEQ ID NO:5 and SEQ ID NO:6;
   b) detecting an amplification product comprising an expanded CAG trinucleotide repeat region, whereby said detection of an expanded CAG trinucleotide repeat having to sequence $(CAG)_n$, wherein $n \geq 30$, is indicative of spinocerebellar ataxia type 7 in said human; and
   c) determining that said human has SCA7 when $n \geq 30$.

* * * * *

UNITED STATES PATENT AND TRADEMARK OFFICE
CERTIFICATE OF CORRECTION

PATENT NO. : 7,118,893 B2  Page 1 of 1
APPLICATION NO. : 10/357322
DATED : October 10, 2006
INVENTOR(S) : Ranum et al.

It is certified that error appears in the above-identified patent and that said Letters Patent is hereby corrected as shown below:

Column 31
Line 67, delete "tat" and insert --that--

Column 32
Line 59, delete "deternnining" and insert --determining--

Column 33
Line 5, delete "reaion" and insert --region--
Line 10, delete "spinocerebeliar" and insert --spinocerebellar--

Column 34
Line 9, delete "to" and insert --the--

Signed and Sealed this

Twenty-sixth Day of December, 2006

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 477
<212> TYPE: DNA
<213> ORGANISM: Homo sapiens

<400> SEQUENCE: 1
cgactctttc ccccttttttt ttgttacatt gtaggagcgg aaagaatgtc ggagcgggcc      60
gcggatgacg tcaggggga gccgcgccgc gcggcggcgg cggcgggcgg agcagcggcc       120
gcccggcagc agcagcagca gcagcagcag cagcagcagc agcagcagca gcagcagcag      180
cagcagcagc agcagcagca gcagcagcag cagcagcagc agcagcagca gcagcagcag      240
cagcagcagc agcagcagca gcagcagcag cagcagcagc agcagccgcc gcctccgcag      300
ccccagcggc agcagcaccc gccaccgccg ccacggcgca cacggccgga ggacggcggg      360
cccggcgccg cctccacctc ggccgccgca atggcgacgg tcggggagcg caggcctctg      420
cccagtcctg aagtgatgct gggacagtcg tggaatctgt gggttgaggc ttccaaa        477

<210> SEQ ID NO 2
<211> LENGTH: 1864
<212> TYPE: DNA
<213> ORGANISM: Homo sapiens
<220> FEATURE:
<221> NAME/KEY: unsure
<222> LOCATION: (1346)
<223> OTHER INFORMATION: Any nucleotide

<400> SEQUENCE: 2
gaattcaagt tccccaggcg cgcacagtgt gacttccaat tgcgggtcgg gggcacacat      60
gtgggcggcg tggcgtgcac acggtacttc gtcctgacac ctgggcagac acctgggagg     120
cacttccccg ctagcccaag gttccctgca cgcccggagt ccgctctgcg gcggcttccc     180
attcatgctt ttgacaactc tgcggccgcc cgcaagccga gggcaaagtg ccccctgcac     240
```

-continued

| | |
|---|---|
| cagcctctcc cgcgctgccc tggggccggc cggccggctc ctccataggt ggctgcattt | 300 |
| ccgacttcgc cctggctcca gtccggggc ttgacgtgca aacttcgccg agcgagctg | 360 |
| agagggaggg accggcaagt gggaggaggc ggcgggaggc gtctccgctt aagggagccg | 420 |
| gccgggtgcc gccgctcgga cggacgcgcg gacggaagga aggagcgggg cagccgggcc | 480 |
| gggcccgggg atgcaagcgg ccgaaggtg ggcagctgga ggtcctgggg tgcggctcgg | 540 |
| gcttccccgc gcgggctgcc atggtgggc gcggggttgg agccgggccg ctccggcgct | 600 |
| ggcctccgcg ccaggtcctc tgagcagaag caggcagggg acccagcgcc gcggtggcgg | 660 |
| gccgcctgct gcccgtcccc tccctcgggc ggccgcggga gtcgaaagcg aaagctagcc | 720 |
| cgcgccgcga cttgagcccg ggcgggggt ggccttgagg aggcgggctc gggggctgg | 780 |
| gcggccatgg gggcgctgtc agcgtgcccc accggtccg cgggccgcgc acgccgccgg | 840 |
| aactccctgg cgcctcctta aaaaacggcc cccgcgcgac tctttccccc ttttttttgt | 900 |
| tacattgtag gagcggaaag aatgtcggag cgggccgcgg atgacgtcag gggggagccg | 960 |
| cgccgcgcgg cggcggcggc gggcggagca gcggccgccc ggcagcagca gcagcagcag | 1020 |
| cagcagcagc agccgccgcc tccgcagccc cagcggcagc agcacccgcc accgccgcca | 1080 |
| cggcgcacac ggccggagga cggcgggccc ggcgccgcct ccacctcggc cgccgcaatg | 1140 |
| gcgacggtcg gggagcgcag gcctctgccc agtcctgaag tgatgctggg acagtcgtgg | 1200 |
| aatctgtggg ttgaggcttc caaacttcct gggaaggacg gtgagtgtcc acgccctcct | 1260 |
| ccccccttca cccccctcgcg accccctcct ctctcctccc ctcccccctg cccccctcct | 1320 |
| gtgacccgcc ccctcgaggg gcaganatgc tatcgtttgc tgggttgcgg aacgcggagg | 1380 |
| tgcccacacc taccccgtgc gtgcgtgagt gtgcgtcaca ctcctggcca ctgacctgcc | 1440 |
| tctcccctcc tcctgtgtgt gtatatctcc taggacagaa ttggacgaaa gtttcaagga | 1500 |
| gtttgggaaa accgcgaagt catggggctc tgtcggaag gtgagtccag ccccctgat | 1560 |
| ggagtttgta caaacccctg ggaagtttca ttgacagttc actgggaccg ggaacatcag | 1620 |
| cccaccatac cgactccccg actcccgtg cctgcgaaga tgctgcctga ggagggaggg | 1680 |
| aggggcaga gcgcttggaa agtttggttt ggggccctcc tgtaatgaga gcgtccggaa | 1740 |
| tccttctgtg accaggcagg agcagcatta ttggtgatga gcgctgggaa ccggcgggaa | 1800 |
| gtttaacata gatctctgca tttctgacct ccttacggag aaacaggagt agaggaagga | 1860 |
| attc | 1864 |

<210> SEQ ID NO 3
<211> LENGTH: 300
<212> TYPE: DNA
<213> ORGANISM: Homo sapiens

<400> SEQUENCE: 3

| | |
|---|---|
| caagcagaaa gggggctgca aagctgcctg cctagggcta cgtttcctgg caaaacttcc | 60 |
| gaaagccatt tctccaaaag aaggtctaga agaggaggag gaggaggaga aggaggagga | 120 |
| ggaggaggag cagcagcagc agcagcagca gcagcagcag cagcagcagc agcagcagca | 180 |
| gcatgaaaga gccccacttg gaaggcggtt tggatttat ttgtgtgttt tgtggattct | 240 |
| ttttattttg ctttacaaat gcatcttaca ccaaactcat ctggcattaa aaatgaattc | 300 |

<210> SEQ ID NO 4
<211> LENGTH: 30
<212> TYPE: DNA
<213> ORGANISM: Homo sapiens

-continued

```
<400> SEQUENCE: 4
cagcagcagc agcagcagca gcagcagcag                                    30

<210> SEQ ID NO 5
<211> LENGTH: 23
<212> TYPE: DNA
<213> ORGANISM: Homo sapiens

<400> SEQUENCE: 5 tttttgtta cattgtagga gcg                                            23

<210> SEQ ID NO 6
<211> LENGTH: 20
<212> TYPE: DNA
<213> ORGANISM: Homo sapiens

<400> SEQUENCE: 6
cacttcagga ctgggcagag                                               20

<210> SEQ ID NO 7
<211> LENGTH: 23
<212> TYPE: DNA
<213> ORGANISM: Homo sapiens

<400> SEQUENCE: 7
gccagatgag tttggtgtaa gat                                           23

<210> SEQ ID NO 8
<211> LENGTH: 24
<212> TYPE: DNA
<213> ORGANISM: Homo sapiens

<400> SEQUENCE: 8
aagccatttc tccaaaagaa ggtc                                          24

<210> SEQ ID NO 9
<211> LENGTH: 129
<212> TYPE: DNA
<213> ORGANISM: Homo sapiens

<400> SEQUENCE: 9
cgactctttc cccctttttt ttgttacatt gtaccaggag cggaaagaat gtcggagcgg    60
gccgcggatg acgtcagggg ggagccgcgc cgcgcggcgg cggcggcggg cggagcagcg   120
gccgcccgg                                                          129

<210> SEQ ID NO 10
<211> LENGTH: 192
<212> TYPE: DNA
<213> ORGANISM: Homo sapiens

<400> SEQUENCE: 10
ccgccgcctc cgcagcccca gccgcagcag caccgccac cgccgccacg gcgcacacgg     60
ccggaggacg gcgggcccgg cgccgcctcc acctcggccg ccgcaatggc gacggtcggg   120
gagcgcaggc ctctgcccag tcctgaagtg atgctgggac agtcgtggaa tctgtgggtt   180
gaggcttcca aa                                                      192

<210> SEQ ID NO 11
<211> LENGTH: 27
<212> TYPE: PRT
```

<213> ORGANISM: Homo sapiens

<400> SEQUENCE: 11

Met Ser Glu Arg Ala Ala Asp Asp Val Arg Gly Glu Pro Arg Arg Ala
1               5                   10                  15

Ala Ala Ala Ala Gly Gly Ala Ala Ala Ala Arg
            20                  25

<210> SEQ ID NO 12
<211> LENGTH: 129
<212> TYPE: PRT
<213> ORGANISM: Homo sapiens

<400> SEQUENCE: 12

Met Ser Glu Arg Ala Ala Asp Asp Val Arg Gly Glu Pro Arg Arg Ala
1               5                   10                  15

Ala Ala Ala Ala Gly Gly Ala Ala Ala Arg Gln Gln Gln Gln Gln
            20                  25                  30

Gln Gln Gln Gln Pro Pro Pro Gln Pro Gln Arg Gln Gln His
        35                  40                  45

Pro Pro Pro Pro Arg Arg Thr Arg Pro Glu Asp Gly Gly Pro Gly
    50                  55                  60

Ala Ala Ser Thr Ser Ala Ala Ala Met Ala Thr Val Gly Glu Arg Arg
65                  70                  75                  80

Pro Leu Pro Ser Pro Glu Val Met Leu Gly Gln Ser Trp Asn Leu Trp
                85                  90                  95

Val Glu Ala Ser Lys Leu Pro Gly Lys Asp Glu Asp Arg Ile Gly Arg
                100                 105                 110

Lys Phe Gln Gly Val Trp Glu Asn Arg Glu Val Met Gly Leu Cys Arg
            115                 120                 125

Glu

<210> SEQ ID NO 13
<211> LENGTH: 1002
<212> TYPE: DNA
<213> ORGANISM: Homo sapiens

<400> SEQUENCE: 13
gaattcaagt tccccaggcg cgcacagtgt gacttccaat tgcgggtcgg gggcacacat       60
gtgggcggcg tggcgtgcac acggtacttc gtcctgacac ctgggcagac acctgggagg     120
cacttccccg ctagcccaag gttccctgca cgcccggagt ccgctctgcg gcggcttccc     180
attcatgctt ttgacaactc tgcggccgcc cgcaagccga gggcaaagtg ccccctgcac     240
cagcctctcc cgcgctgccc tggggccggc cggccggctc ctccataggt ggctgcattt     300
ccgacttcgc cctggctcca gtccgggggc ttgacgtgca aacttcgccg gagcgagctg     360
agagggaggg accggcaagt gggaggaggc ggcgggaggc gtctccgctt aagggagccg     420
gccgggtgcc gccgctcgga cggacgcgcg gacggaagga aggagcgggg cagccgggcc     480
gggcccgggg atgcaagcgg ccgaaggtg gcagctgga ggtcctgggg tgcggctcgg      540
gcttccccgc gcgggctgcc atggtgggc gcggggttgg agccgggccg ctccggcgct      600
ggcctccgcg ccagtcctc tgagcagaag caggcagggg acccagcgcc gcggtggcgg      660
gccgcctgct gcccgtcccc tccctcgggc ggccgcggga gtcgaaagcg aaagctagcc      720
cgcgccgcga cttgagcccg gggcgggggt ggccttgagg aggcgggctc ggggggctgg      780
gcggccatgg gggcgctgtc agcgtgcccc acccggtccg cgggccgcgc acgccgccgg      840

```
aactccctgg cgcctcctta aaaaacggcc cccgcgcgac tctttccccc ttttttttgt      900
tacattgtag gagcggaaag aatgtcggag cgggccgcgg atgacgtcag gggggagccg      960
cgccgcgcgg cggcggcggc gggcggagca gcggccgccc gg                       1002

<210> SEQ ID NO 14
<211> LENGTH: 832
<212> TYPE: DNA
<213> ORGANISM: Homo sapiens
<220> FEATURE:
<221> NAME/KEY: unsure
<222> LOCATION: (314)
<223> OTHER INFORMATION: Any nucleotide

<400> SEQUENCE: 14
ccgccgcctc cgcagcccca gcggcagcag caccegccac cgccgccacg gcgcacacgg       60
ccggaggacg gcgggcccgg cgccgcctcc acctcggccg ccgcaatggc gacggtcggg      120
gagcgcaggc ctctgcccag tcctgaagtg atgctggac agtcgtggaa tctgtgggtt       180
gaggcttcca aacttcctgg gaaggacggt gagtgtccac gccctcctcc ccccttcacc      240
ccctcgcgac cccctcctct ctcctcccct ccccctgcc ccctcctgt gacccgcccc       300 ctcgaggggc aganatgcta tcgtttgctg ggttgcggaa cgcggaggtg cccacaccta      360
ccccgtgcgt gcgtgagtgt gcgtcacact cctggccact gacctgcctc tcccctcctc      420
ctgtgtgtgt atatctccta ggacagaatt ggacgaaagt ttcaaggagt ttgggaaaac      480
cgcgaagtca tggggctctg tcgggaaggt gagtccagcc ccctgatgg agtttgtaca      540 aaccctggg aagtttcatt gacagttcac tgggaccggg aacatcagcc caccatacg      600 actccccgac tccccgtgcc tgcgaagatg ctgcctgagg agggaggag ggggcagagc       660 gcttggaaag tttggtttgg gggcctcctg taatgagagc gtccggaatc cttctgtgac      720
caggcaggag cagcattatt ggtgatgagc gctgggaacc ggcgggaagt ttaacataga      780
tctctgcatt tctgacctcc ttacggagaa acaggagtag aggaaggaat tc             832
```